United States Patent [19]
Burdea et al.

[11] Patent Number: 5,354,162
[45] Date of Patent: Oct. 11, 1994

[54] ACTUATOR SYSTEM FOR PROVIDING FORCE FEEDBACK TO PORTABLE MASTER SUPPORT

[75] Inventors: Grigore C. Burdea, Highland Park; Daniel Gomez, Piscataway, both of N.J.

[73] Assignee: Rutgers University, New Brunswick, N.J.

[21] Appl. No.: 937,654

[22] Filed: Aug. 31, 1992

Related U.S. Application Data

[63] Continuation-in-part of Ser. No. 661,515, Feb. 26, 1991, Pat. No. 5,143,505.

[51] Int. Cl.⁵ .............................................. B25J 13/02
[52] U.S. Cl. .......................................... 414/5; 414/4
[58] Field of Search ................... 414/5, 4, 6; 623/63, 623/64; 244/234

[56] References Cited

U.S. PATENT DOCUMENTS

| | | |
|---|---|---|
| 3,171,549 | 3/1965 | Orloff . |
| 3,263,824 | 8/1966 | Jones et al. . |
| 3,414,137 | 12/1968 | Fortin . |
| 3,449,008 | 6/1969 | Colechia . |
| 3,618,786 | 11/1971 | Fick . |
| 3,637,092 | 1/1972 | George et al. . |
| 3,771,037 | 11/1973 | Bailey, Jr. . |
| 3,995,831 | 12/1976 | Spanski et al. . |
| 4,302,138 | 11/1981 | Zarudiansky . |
| 4,604,016 | 8/1986 | Joyce . |
| 4,795,296 | 1/1989 | Jau . |
| 5,004,391 | 4/1991 | Burdea .................................. 414/6 |

OTHER PUBLICATIONS

Paper presented at the "Symposium on Dynamics and Control of Biomechanical Systems":, Dec. 1989 at the ASME winter annual meeting by the inventor.

*Primary Examiner*—Donald W. Underwood
*Attorney, Agent, or Firm*—Mathews, Woodbridge & Collins

[57] ABSTRACT

An actuator system provides force feedback to a master support. A first, second and third digit support are connectable by a finger mount to the thumb, index and middle, and ring digits, respectively. First, second, third and fourth actuators comprising pneumatic cylinders extend between the first, second, third and fourth digit supports and an "L" shaped palm support mountable on the palm of the glove. Sensors are mounted to the pneumatic cylinders to provide electrical signals on the positioning of the fingers. The signals are forwarded by a stand alone feature to a host computer. The host computer computes the positioning of the finger and provides feedback through interface to the first, second and third actuators. Azimuthal mounts connect the first, second, third and fourth actuators to the palm support for increased movement of the digits.

16 Claims, 17 Drawing Sheets

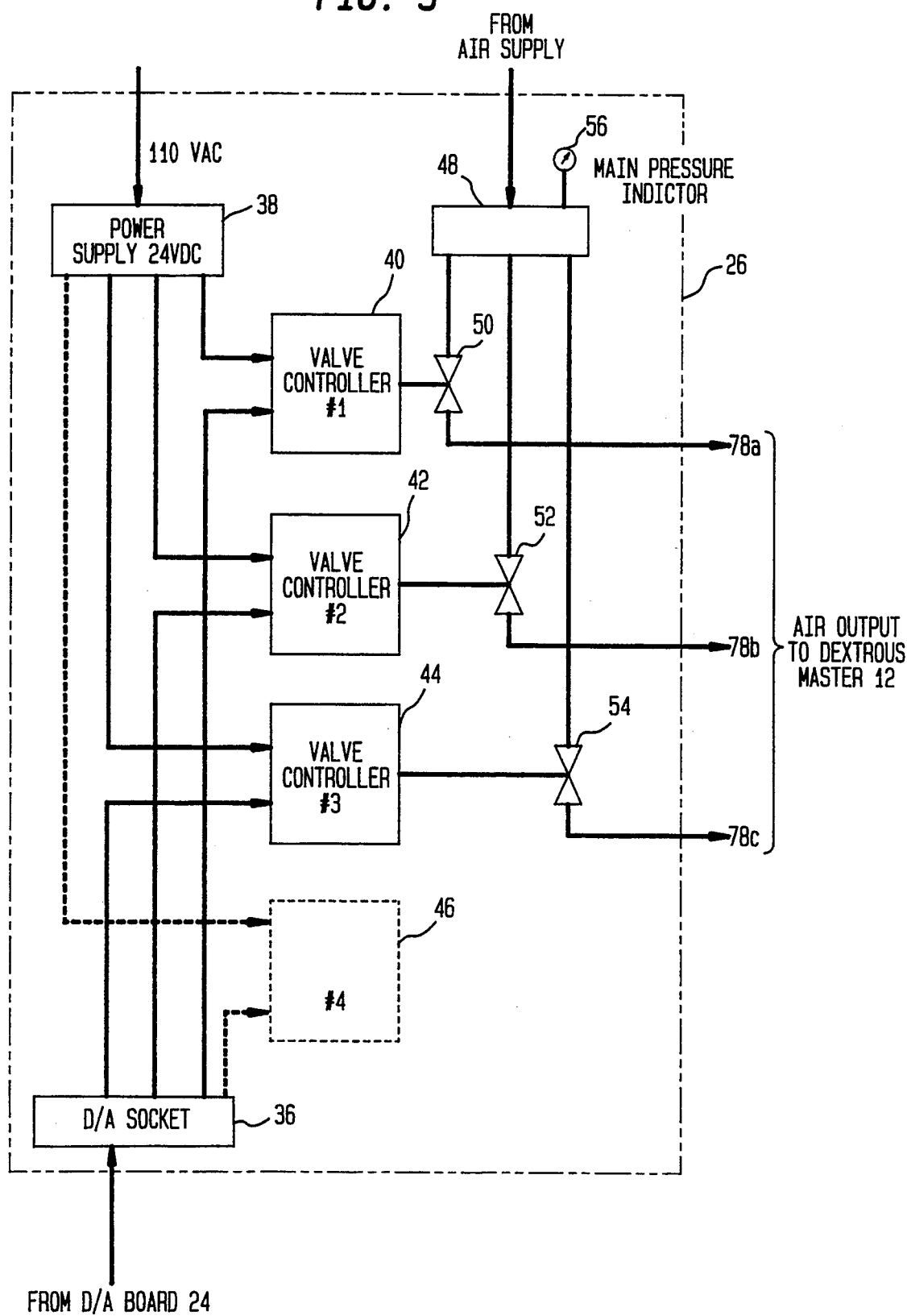

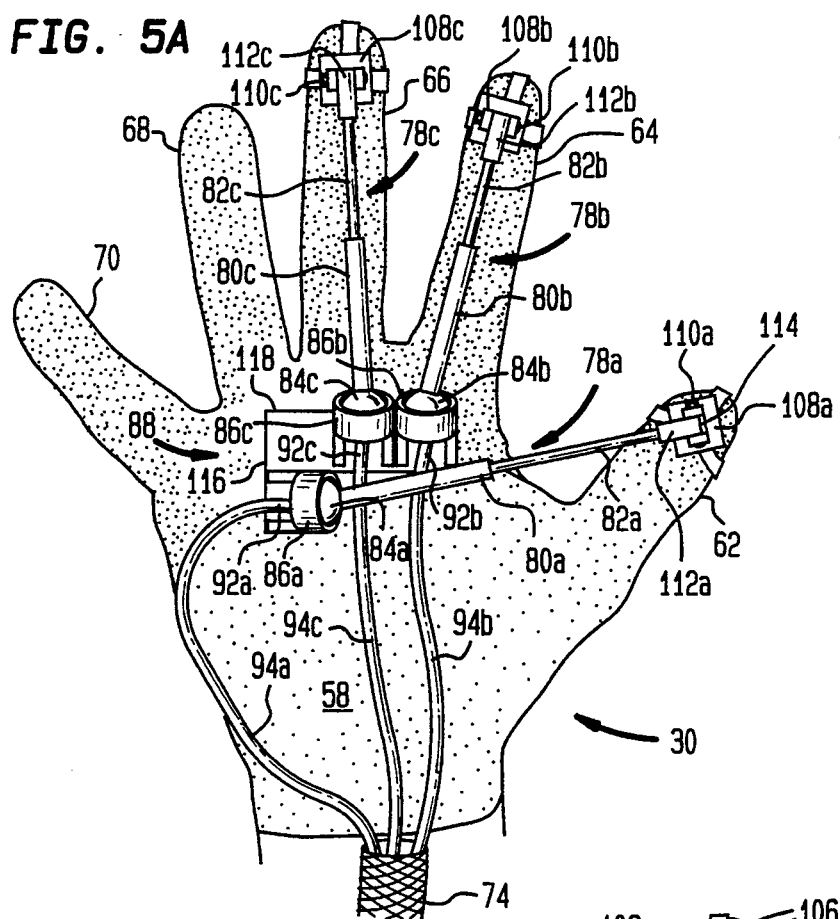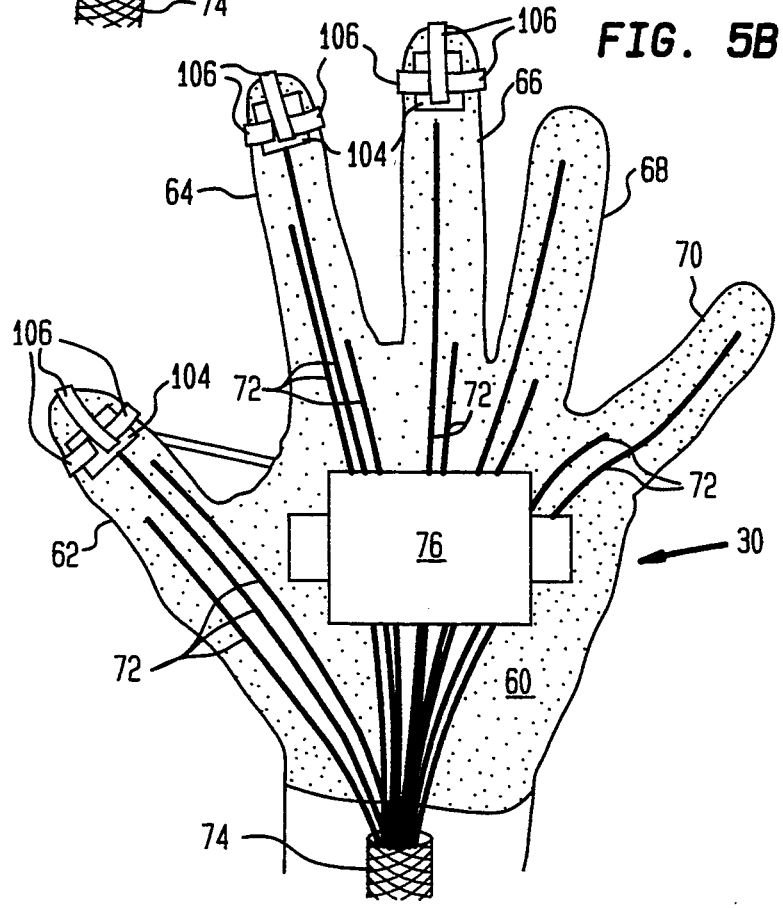

ACTUATOR SYSTEM FOR PROVIDING FORCE FEEDBACK TO PORTABLE MASTER SUPPORT

CROSS-REFERENCE TO RELATED INVENTIONS

This application is related to U.S. patent application Ser. No. 07/396,476 filed Aug. 21, 1989 now U.S. Pat. No. 5,004,391 by Grigore C. Burdea and entitled PORTABLE DEXTROUS FORCE FEEDBACK MASTER FOR ROBOT TELEMANIPULATION and is a continuation-in-part of copending U.S. patent application Ser. No. 07/661,515, filed Feb. 26, 1991 and entitled "ACTUATOR SYSTEM FOR PROVIDING FORCE FEEDBACK TO A DEXTROUS MASTER GLOVE", the entire text and contents of both of which are hereby incorporated by reference into this application

BACKGROUND OF THE INVENTION

1. Field of the Invention

This invention relates to an actuator system for providing force feedback to a portable master support as a function of manipulation of an interactive system.

2. Description of Related Art

Present telemanipulation techniques include the use of mechanical masters, open-loop servomasters, and to a lesser extent, closed-loop servomasters. Direct mechanical telemanipulation is often the simplest method, but cannot be used in applications where the slave is not in the immediate vicinity of the master. Closed-loop telemanipulation eliminates the proximity requirement but may necessitate the need to have two nearly identical devices to act as master and slave. This duplication of resources is often prohibitive in terms of cost and payload weight.

Efforts have been made to eliminate the duplicate master by replacing it with force feedback joysticks, sensorized spheres, pistol grips and the like. Although such devices have served their purposes, they have not proved entirely satisfactory under all conditions of service because these devices are less "natural" to an operator since direct similitude does not exist between human hand and robot finger motions. Examples of manual controllers using levers, grippers, handles and the like, with some having force feedback, may be found in the following U.S. Pat. Nos.: 4,795,296; 3,995,831; 4,604,016; 3,618,786; 3,637,092 and 3,771,037.

Those concerned with the development of telemanipulation devices have recognized the disadvantages of such prior art controllers and the need for a dextrous master controller that uses an operator's hand to replace the classical manipulation arm, the conventional keypad contact, the joystick or handle, or other similar structure. Use of the human hand is a natural form of control and is applicable for use with both non-dextrous and dextrous slave devices. Further, because the human hand is used as master, duplication of most hardware is not required and weight, inertia and friction can be reduced. Under most conditions, significant improvements in the time necessary to complete a task can be realized when using the human hand as the master. For example, it has been estimated that an improvement on the order of 10 can be expected on time efficiency when a dextrous master is used in place of a conventional keypad control.

While open-loop dextrous masters create more natural control environments, they lack the ability to bring force feedback to the operator's hand, which in turn limits the utility of the slave device. However, a dextrous master with force feedback, using much of the human hand as master in a closed-loop teleoperations environment, will allow the efficient execution of complex tasks such as assembly and repair involving the telemanipulation of small, intricately-shaped parts. Examples of robotic masters with force feedback and wherein much of the human hand is used as the master may be found in the following U.S. Pat. Nos.: 3,449,008; 3,171,549 and 4,302,138.

U.S. Pat. Nos. 3,414,137 entitled REMOTE HANDLING DEVICE issued Dec. 3, 1968 to Marcel Fortin is typical of telemanipulation devices that employ a squeezable, manipulatable device for remote control. A hand grabbable grip is squeezed causing the remote flexing of a pair of robotic fingers around an object. This device is especially adapted for use in nuclear reactors or dangerous environments.

U.S. Pat. No. 4,302,138 entitled REMOTE HANDLING OF DEVICES issued on Nov. 24, 1981 to Alain Zarudiansky, describes a device for improving the grip and remote handling of an object. An artificial hand, or slave hand, is remotely controlled by the hand of an operator. Sensors on the artificial hand provide for the sensing of tactile parameters. The signals produced by the sensors are applied to actuators located on the backside of the master hand. The master hand may be in the form of a modified glove in which the hand of the operator is inserted. The actuators mounted on the backside glove supply tactile sensations to the hand of the operator. Thus the operator apparently "feels" the object as if the object were being handled directly by the operator. This particular device is especially useful for the handling of objects in dangerous environments, such as in the nuclear or chemical industries, or possibly may be used by an operator in outer space or underwater. The major drawback of such a device is that it is fairly bulky because it requires the sensing and manipulation of the hand from the backside. The hand thus loses a lot of its "feel" because the "feel" of a hand is from the palm not the outside. Thus, the device such as set forth in U.S. Pat. No. 4,302,138 is significantly larger and less effective than the device set forth in the present disclosure.

The foregoing examples demonstrate various prior art attempts to obtain a controller that is more "natural" to the operator. There has been long recognized a need for "natural" dextrous masters that more closely simulate the motions of the finger of a dextrous slave. Unfortunately, no practical system has yet been devised for doing so. Ideally, such a system would have the capability of being hand-holdable in an actual position in the operator's hand. It would also be operable by the operator using natural motions and would be relatively lightweight. A force feedback mechanism would be provided back to the operator's hand in a manner that corresponds directly to the forces generated on the slave. Moreover, the device should be compact, portable, simple in construction and dependable in operation, and safe for the operator.

In an attempt to solve the foregoing challenges, one of the inventors discovered a technique and mechanism set forth in U.S. application Ser. No. 07/396,476 now U.S. Pat. No. 5,004,391 and entitled PORTABLE DEXTROUS FORCE FEEDBACK MASTER FOR ROBOT TELEMANIPULATIONS, the entire contents of which is incorporated by reference into this disclosure. The actuator device described therein includes a compact, hand-held unit that fits within the space defined by the user's palm and fingers and functions as a position controller for a robot having a slave hand. A finger position sensor including a linear, variable differential transformer provides an output signal that is proportional to the distance between the user's fingers. A force feedback system, including a pneumatic micro-actuator, senses the forces exerted by the end effectors of the robot hand and causes a corresponding force to be exerted on the fingers of the user. The foregoing invention was intended primarily for use between the thumb and middle finger of the operator's hand. As such, it limited the ability to provide force feedback between any other fingers of the hand and also required the usage of a special sensor system using a linear differential transformer between the two manipulating digits. However, there now exists on the market sensor-type gloves such as the DataGlove ™ Model 2 available from VPL Research, Inc., 950 Tower Lane, 14th Floor, Foster City, Calif. 94404 which senses the position of the fingers and provides information with regard to position and orientation to a host computer for a variety of different purposes. A Polhemus-type sensor mounted on the backside of the glove, provides information with regard to the motion of the wrist in space. Sensor gloves such as the DataGlove ™ typically include fiber optic sensors that are located on the back, i.e. topside, of the glove such that the movement of the fingers is sensed by the fiber optic sensors and transmitted through a fiber optic umbilical bundle back to a glove interface. The glove interface suitable for use with a standard host computer is also available from VPL Research, Inc.

The concept of employing a sensor-type glove in the context of a force feedback system was described in a paper presented at the "Symposium on Dynamics and Control of Biomechanical Systems" December 1989 at the ASME winter annual meeting by the primary inventor.

U.S. Pat. No. 3,171,549 entitled "MECHANICAL HANDLING APPARATUS" issued Mar. 2, 1965 to G. Orloff was cited during prosecution of the patent application Ser. No. 07/661,515. An apparatus includes a pistol grip and finger grips. Hydraulic bellows actuators provides "feel feedback" to the finger grips. This device has the disadvantage of being bulky and less effective than the device set forth in the present invention.

SUMMARY OF THE INVENTION

Briefly described, the invention comprises an actuator system for providing force feedback to a dextrous master device. The master device typically includes a plurality of fiber optic sensors located on the backside of the glove for detecting movement of the digits. A hand is considered to have five digits, namely four fingers (index, middle, ring and small fingers) and an opposed thumb. A linkage or a Polhemus-type sensor can be mounted on the back of the glove to provide information with regard to the position and orientation of the wrist. While such devices are adequate for the purpose of providing sensory input to computers with regard to the movement of the hand and digits, the use of such devices with force feedback mechanisms that provide a "natural" feel is limited. According to the present invention, a first, second and third digit support are connectable by hook and loop fasteners to the thumb, index and middle digits of the glove, respectively. The hook and loop fasteners are preferably of the well-known Velcro ® variety manufactured by Velcro USA, Inc., 406 Brown Avenue, Manchester, N.H. 03108. First, second and third actuators comprising pneumatic cylinders extend between the first, second and third digit supports and an "L" shaped palm support mountable on the palm of the glove. The "L" shaped palm support has a first leg and a second leg. Sphere-type joints connect the first, second and third actuators to the "L" shaped palm support. The actuator between the thumb and the palm support is connected by its sphere joint to the first leg of the "L" shaped palm support. The other two actuators connected between the index finger and middle finger to the palm support both share the second leg of the "L" shaped palm support in common. Each sphere joint includes an air passageway that communicates with the pneumatic force feedback cylinder in the actuators. Pin type cylindrical joints connect the first, second and third digit supports to the first, second and third actuators. The sensors mounted on the back of the master glove provide electrical signals that are interpreted by a conventional glove interface, available commercially, and forwarded to a commercially available UNIX ®based host computer. UNIX ® is a trademark of AT&T Bell Laboratories. The host computer computes the movement of the glove and provides force feedback instructions through a digital-to-analog circuit and an actuator interface to the first, second and third actuators, respectively.

The spherical joints permit the rotation of the thumb, index and middle fingers in a cone of about 60°. Because all of the actuators are mounted between the digits and the palm, it provides for a realistic, natural feeling response as a result of the remote manipulation of an object by a robot slave hand or by a virtual hand. The device is also more realistic in that it is compact and easy to use.

In an alternate embodiment of the invention an actuator system is provided without the use of a dextrous master glove. The actuator system includes a first, second, third and fourth digits and "L" shaped palm support. Sensors are mounted in the pneumatic cylinders for providing information in the movement of the digits. A digit mount has a velcro band and a semicircular frame for connecting the cylinder to the digit. A mount connects the pneumatic cylinders to the palm support to provide movement about two perpendicular axis with the degrees of freedom having declination angle $\psi$ and azimuthal angle $\phi$. A rotary position sensor provides information on the declination and azimuthal angles. A polhemus sensor is attached to the back of the hand with a hook and loop fastener. A stand alone interface receives information from the cylinder rotary and linear position sensor and polhemus sensor which information can be forwarded to a host computer. An air compressor and pressure regulator are part of the interface for providing force feedback to the actuator system. In this embodiment, the invention is intended primarily for virtual reality applications.

The foregoing features will be better understood by reference to the following drawings.

BRIEF DESCRIPTION OF THE DRAWINGS

FIG. 3 is a block diagram illustrating the components of the actuator interface.

FIG. 5A is a front elevational view of the actuator system in the palm of the dextrous master glove.

FIG. 5B is a rear elevational view of the actuator system and glove illustrated in FIG. 5A.

DETAILED DESCRIPTION OF THE INVENTION

During the course of this description, like numbers will be used to identify like elements according to the different views that illustrate the invention.

Figure 1:
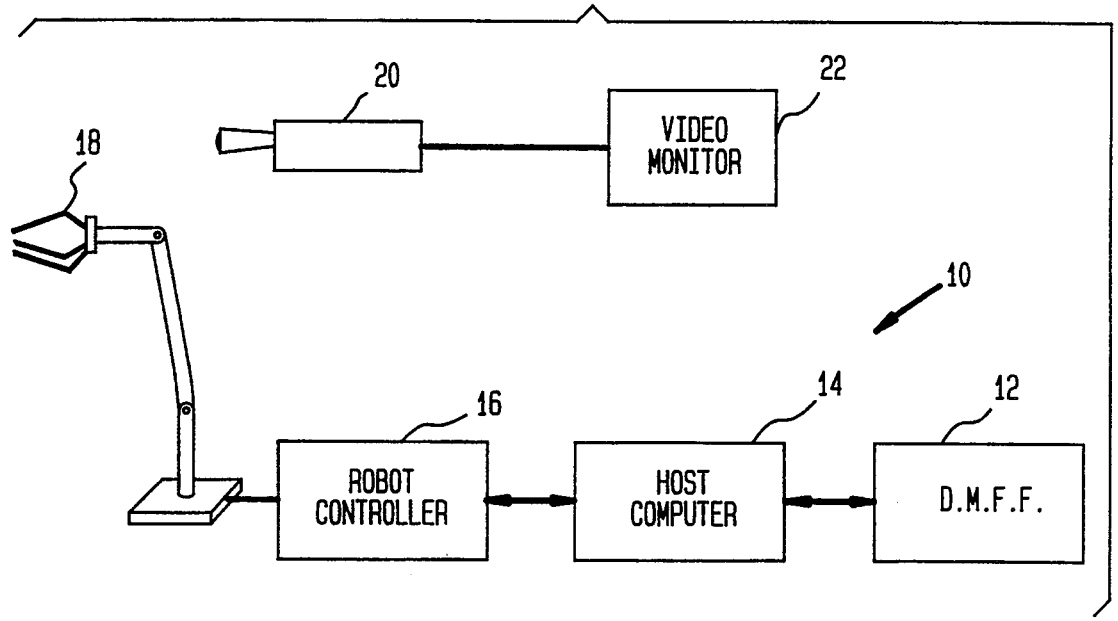
FIG. 1 is a schematic block diagram of the preferred environment of the invention showing the dextrous master with force feedback (D.M.F.F.) manipulating a remote slave hand and providing visual feedback to the operator through a video monitor system.

FIG. 1 illustrates the preferred environment 10 of the invention 12. A dextrous master glove having force feedback ("D.M.F.F.") 12 provides input to a conventional host computer 14. The host computer 14 can be almost any commercially available UNIX based system. In the preferred environment 10, a Model SUN 4-260 SPARC TM station from Sun Microsystems, 2550 Farcia Avenue, Mountain View, Calif. 94043 was employed. The preferred embodiment of the D.M.F.F. 12 is illustrated in further detail in FIGS. 4–5E. Host computer 14 receives signals from the sensors on the D.M.F.F. 12 and converts them into control signals for robot controller 16. A slave hand 18 responds to the instructions from the robot controller 16 to duplicate the motions of the D.M.F.F. 12. Conventional sensors, not shown but known to those of ordinary skill in the art, respond to reaction pressures exerted on the slave hand 8 by objects to be grasped. The reaction signals are transmitted back through robot controller 16 and host computer 14 as force feedback instructions to the D.M.F.F. 12. The preferred embodiment of the environment 10 may also include a video camera 20 and a video monitor 22 to provide visual feedback to the operator 34 as illustrated in FIG. 2B.

Figure 2A:
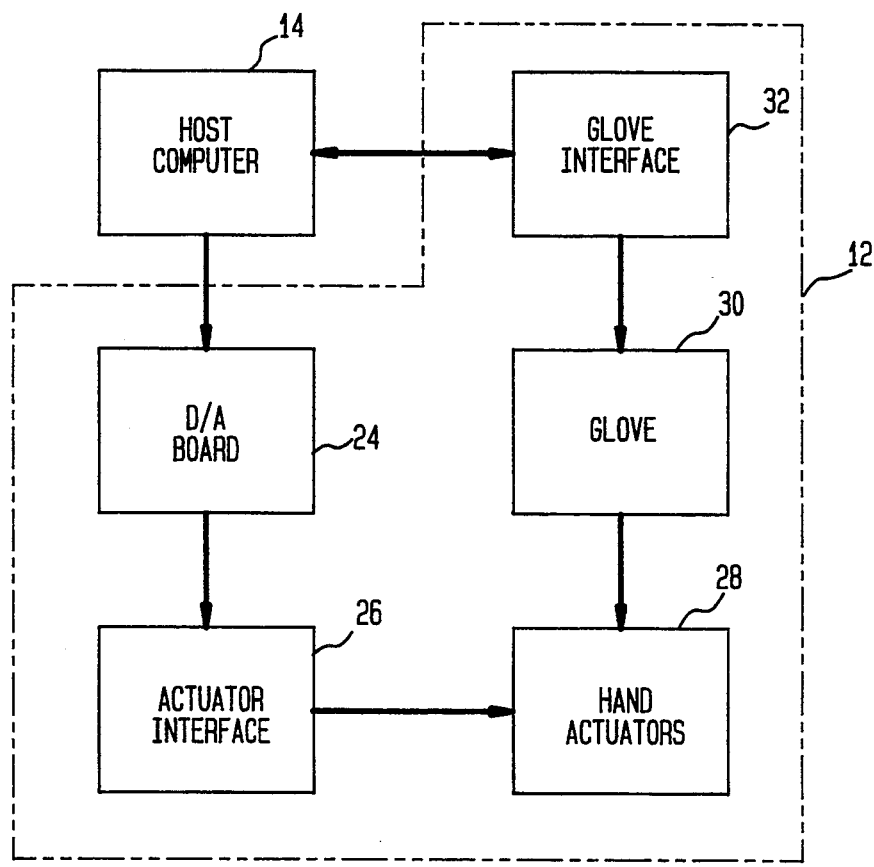
FIG. 2A is a block diagram illustrating the overall system of the present invention.

FIG. 2A is a block diagram which illustrates the details of the D.M.F.F. system 12 as it interacts with host computer 14. The operator 34 begins by placing his or her hand in a glove 30 having sensors mounted on the back. A glove 30 acceptable for the purpose is the Data-Glove TM Model 2, previously disclosed. Fiber optic sensors 72 mounted on the back of the glove 30 create signals which pass through an umbilical cord 74 to a glove interface 32. The sensors 72 measure the movement and position of each of the five digits. A Polhemus-type sensor 76 mounted on the back 60 of the glove 30 provides information with respect to the orientation and position of the wrist. According to the preferred environment 10, a Model "3 space Isotrack" sensor made by Polhemus Navigation Sciences, Colchester, Vermont was employed. An acceptable glove interface 32 is also manufactured by VPL Research, Inc. Digit position and hand orientation are relayed through glove interface 32 to the host computer 14. Host computer 14 acts as a gateway to transmit instructions to a robot hand 18 in an environment such as set forth in FIGS. 1, 6 or 7. Feedback forces responding to the pressure exerted by the slave hand 18 are transmitted back through the host computer 14 to a conventional digital-to-analog circuit board 24. The analog signals from D/A board 24 direct the actuator interface 26 to supply pneumatic pressure to the hand actuator system 28 located in the palm 58 of the sensor glove 30. Details of the actuator interface 26 are described in FIG. 3. The actuators 78a, 78b and 78c that comprise the actuator system 28 provide force feedback to the thumb 62, index 64 and middle 66 fingers of the sensor glove 30. The force feedback is very natural and simulative of the real experience an operator 34 would have if he or she directly manipulated the remote object handled by the robot slave hand 18.

Figure 2B:
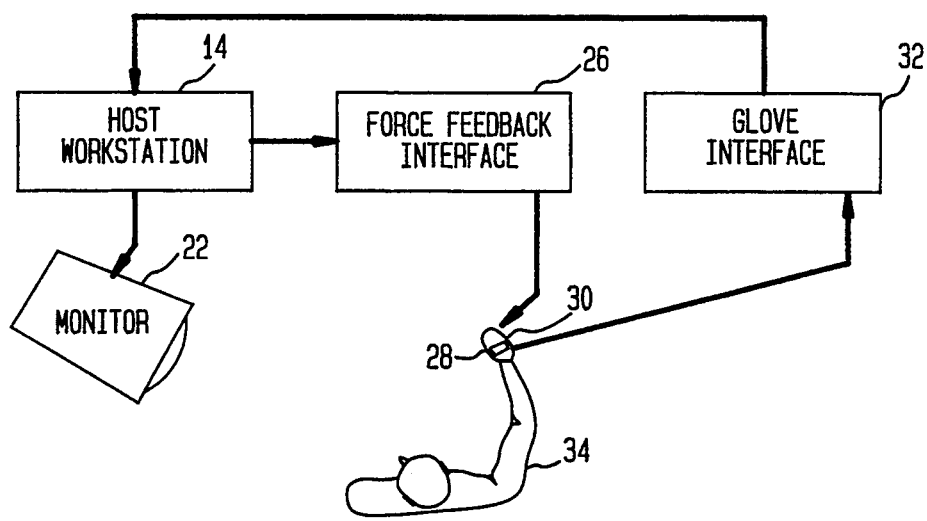
FIG. 2B is another block diagram illustrating the overall system of FIG. 2A under the control of a human operator.

FIG. 2B illustrates the preferred environment 10 of the invention shown in FIG. 1 with an operator 34 in position in front of monitor 22.

Figure 2C:
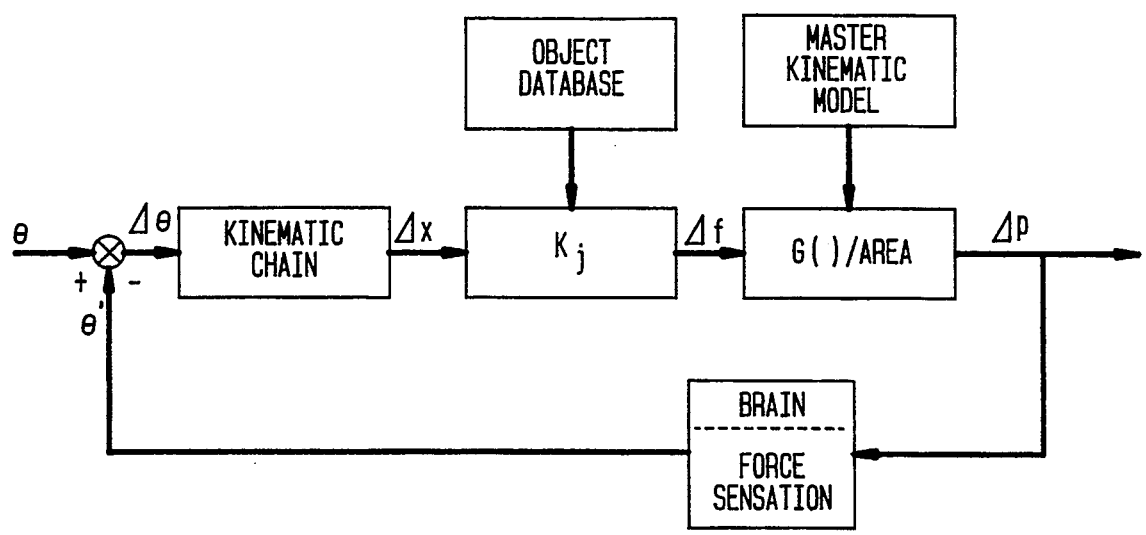
FIG. 2C is a closed control loop block diagram of the system illustrated in FIGS. 2A and 2B.

FIG. 2C is a simplified schematic representation of the closed control loop of the force feedback system. Data $\Delta\theta$ from the sensors 72 and 74 mounted on the back or topside 60 of glove 30 provide input to a feedback point. That data $\Delta\theta$ is transformed $\Delta x$ into linear information and compared against an object data base to produce a desired force $\Delta f$. That information is then compared against a master kinematic model to produce the appropriate change in pressure $\Delta P$ in the actuator structure 28. Force sensation to the feedback point contributes to the operator's decision making, determining a new angle $\theta'$. There may also be visual feedback to the operator's brain by means of a video camera 20 and a video monitor 22 such as illustrated in FIGS. 1 and 2B.

Details of the actuator interface 26 are shown in the block diagram of FIG. 3. Analog signals from the digital-to-analog board 24 are received by D/A socket 36 and are passed as control signals to valve controller #1 (40), valve controller #2 (42), valve controller #3 (44) and, if desired, a valve controller #4 (46). Valve controller 46 is used when four digits are provided with force feedback (i.e. when a structure with four actuators is used). 110V AC power is stepped down by power supply 38 to 24V DC and provides the other input to valve controllers 40, 42, 44 and 46. Air pressure is provided through manifold 48 to pneumatic valves 50, 52 and 54 which are controlled, respectively, by valve controllers 40, 42 and 44. Analog signals from the digital-to-analog board 24 pass through the D/A socket 36 to control valve controllers 40, 42 and 44 which in turn direct valves 50, 52 and 54, respectively, to pass pressurized air to actuators 78a, 78b and 78c. Main pressure indicator gauge 56 measures the pressure in the manifold 48 in order to insure that it is sufficiently high to drive the hand actuator system 28.

Figure 4:
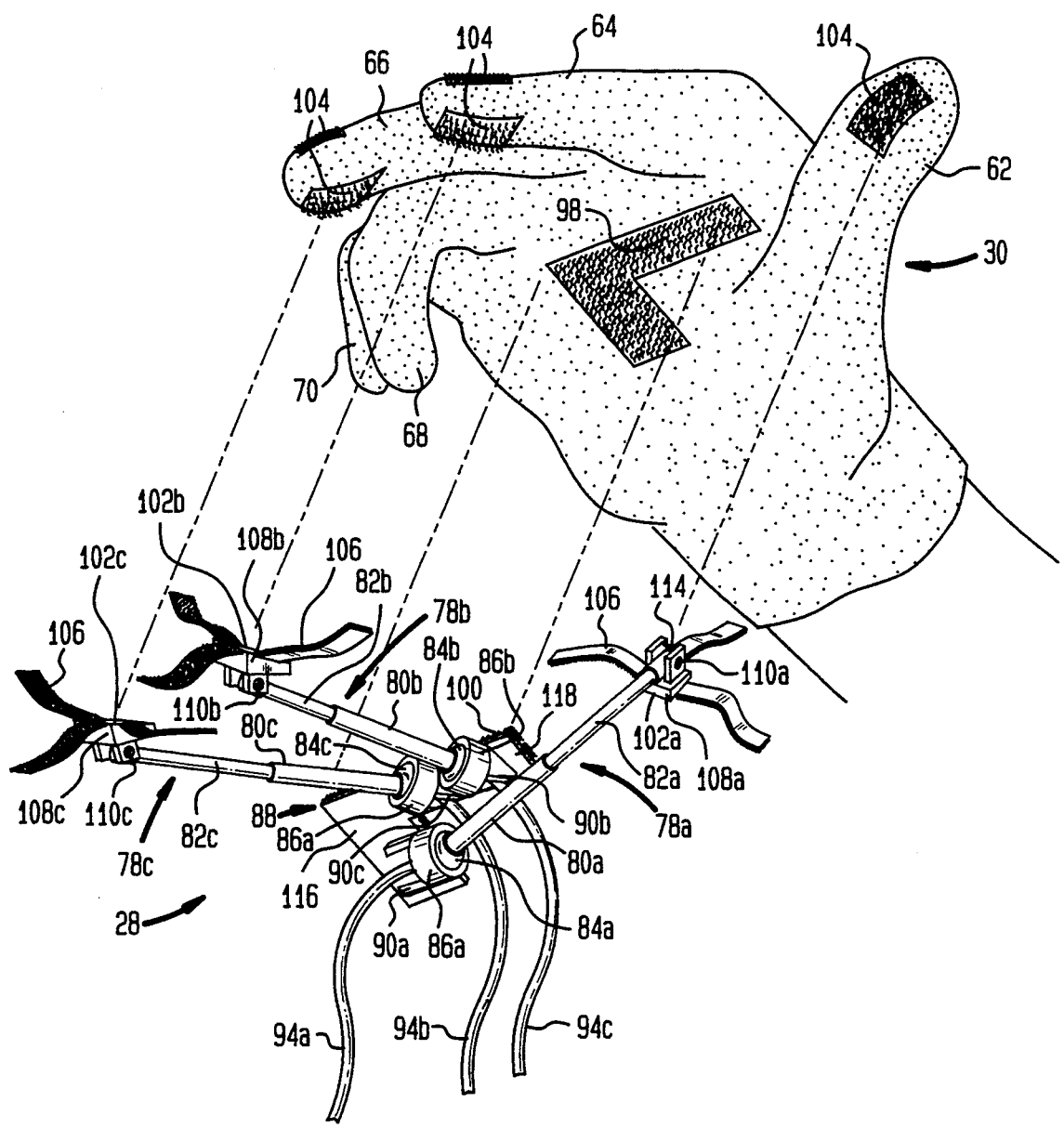
FIG. 4 is an exploded view of the preferred embodiment of the actuator system in the context of a dextrous master glove having sensors mounted on the back thereof.

FIG. 4 is an exploded view of the hand actuator system 28 and glove 30 as seen from below the palm 58 of the glove 30. The glove 30, preferably like the DataGlove TM, previously described, includes a thumb digit 62, an index finger digit 64, a middle finger digit 66, a fourth or ring finger digit 68 and a little finger digit 70. Conventional fiber optic sensors 72 are mounted on the backside of the digits 62-70 as shown in FIG. 5B. The output from the optical sensors 72 passes through an umbilical cord 74 to the glove interface 32. A Polhemus sensor 76 may be mounted on the back 60 of the glove 30. Polhemus sensor 76 works in conjunction with an externally generated electromagnetic field to provide input relative to the position and orientation of the wrist of the operator 34. Leads from the fiber optic sensors 72 and the Polhemus sensor 76 as well as the pneumatic hoses 94a, 94b and 94c all pass through the same umbilical cord 74 for convenience.

The hand actuator system 28 is located in the palm 58 of the glove 30 and comprises three actuators 78a, 78b and 78c which can apply pressure from the palm 58 against the thumb digit 62, index finger digit 64 and the middle finger digit 66, respectively.

The hand actuator system 28 is mounted on an "L" shaped base 88 having two legs 116 and 118. The first leg 116 is shorter than the second leg 118 and at right angles thereto. A sphere joint mounting block 90a supports a sphere joint housing 86a which, in turn, surrounds a sphere joint 84a. As shown in FIG. 5E, a pass through pneumatic fitting 92a accommodates pneumatic hose 94a which passes through sphere joint 84a to cylindrical body 80a of actuator 78a. A movable piston rod 82a sits within cylindrical body 80a. A pin engaging head 112a sits on top of piston rod 82a and engages a cylindrical pin 110a mounted on wedge-shaped mounting section 108a as can be seen in FIGS. 4 and 5A. Wedge-shaped mounting section 108a is, in turn, mounted on the thumb digit base 102a.

In a similar fashion, the other two sphere mounting blocks 90b and 90c are mounted in parallel on the long second leg 118 of the "L" shaped base 88. Sphere joint housings 86b and 86c are supported by the sphere joint mounting blocks 90b and 90c and enclose sphere joints 84b and 84c. Each of the sphere joints 84b and 84c includes a pass through pneumatic fitting 92b and 92c for pneumatic hoses 94b and 94c, respectively, from the actuator interface 26 as illustrated in FIGS. 2A and 3. The air supplied by interface 26 passes through the sphere joints 84b and 84c into the cylindrical bodies 80b and 80c of actuators 78b and 78c. Piston rods 82b and 82c fit within cylindrical bodies 80b and 80c and are adapted to move in and out in response to the air pressure from the actuator interface 26. Piston rods 82b and 82c are equipped with pin engaging heads 112b and 112c which attached to cylindrical pins 110b and 110c for movement in a two-dimensional plane with respect to each digit to which it is attached. Cylindrical pins 110b and 110c are mounted on wedges 108b and 108c which, in turn, are attached to the index and middle bases 102b and 102c, respectively. Wedge or prism-shaped elements 102a, 102b and 102c ensure that the feedback pressure supplied to the digits 62, 64 and 66 is relatively perpendicular to the tips of those digits where a grasping motion is executed. The cylindrical bearing pins 110a, 110b and 110c in combination with the pin engaging heads 112a, 112b and 112c are essentially identical except that the thumb wedge 108a includes a stop bar element 114 to prevent the thumb digit 62 from bending too far with respect to the thumb actuator 78a.

The actuator system 28 is preferably separable from the sensor glove 30. According to the preferred embodiment, hook-type material 100 is attached to the bottom of the "L" shaped base 88 and is adapted to selectively mate with hook-type material 98 located in the palm 58 of glove 30. Similarly, loop-type material 104 on the palm side upper surface of thumb digit 62, index finger digit 64 and middle finger digit 66 are adapted to mate with a hook-type material 106 on the bottom of bases 102a, 102b and 102c. The hook-type material 106 may also pass around to the top or backside of the upper digits 62, 64 and 66 so that a "T" shaped piece of hook material 106 can wrap around to the backside of the digits for better engagement with another piece of loop material 104.

Details of the hand actuator system 28 in the context of a sensor glove 30 are shown in FIGS. 5A and 5B, respectively. FIG. 5A is a front view of the hand actuator system 28 shown mounted on the palm 58 of glove 30. Conversely, FIG. 5B is a rear view of the same glove 30 with the actuator system mounted on the back 60.

Figure 5C:
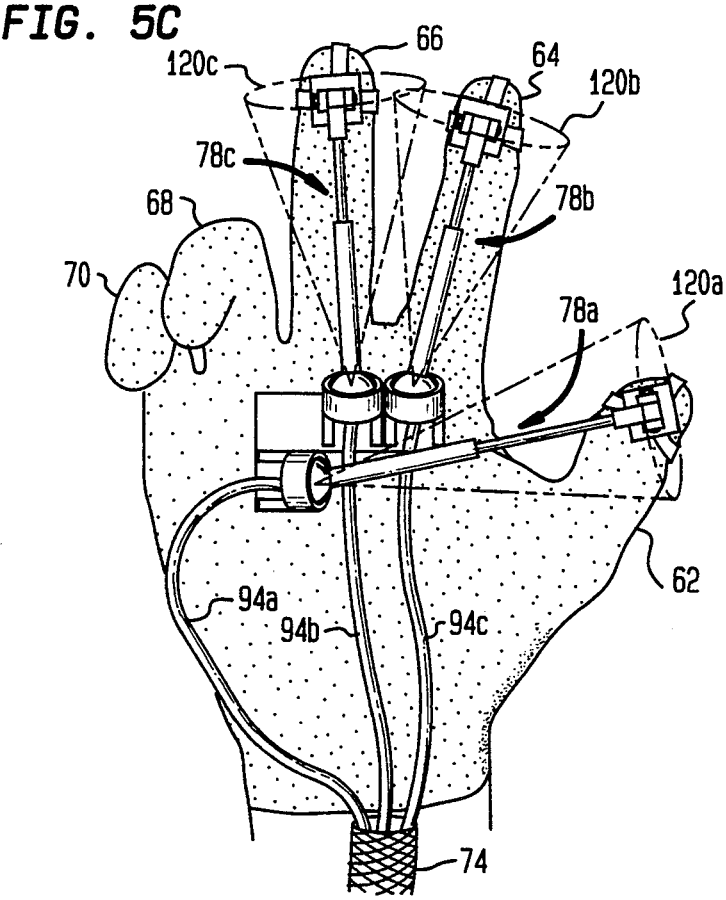
FIG. 5C is a frontal view illustrating the cones of rotation available to the thumb, index and middle fingers using the actuator system according to the present invention.
Figure 5D:
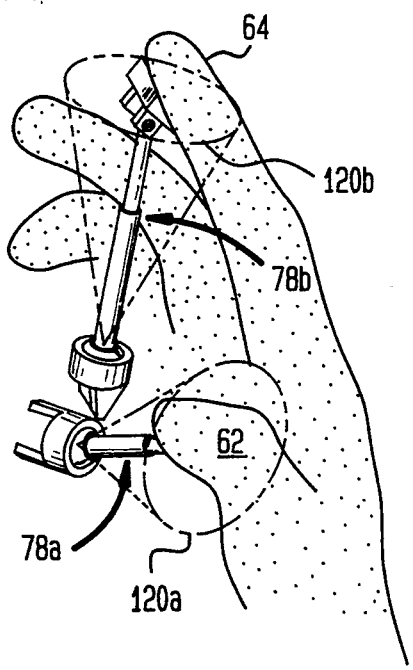
FIG. 5D is a lateral view of the cones of rotation illustrated in FIG. 5C.
Figure 5E:
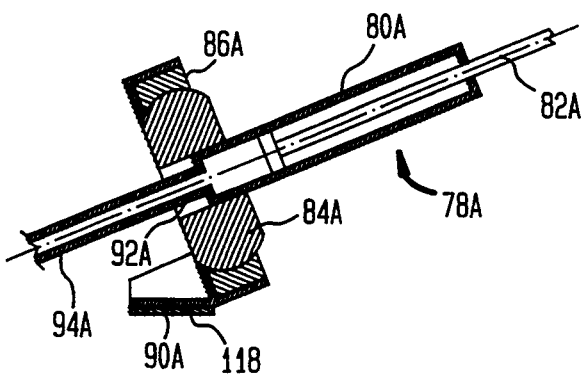
FIG. 5E is a detail cross-sectional view of a single sphere joint showing the air passageway therethrough.

FIGS. 5C and 5D, respectively, illustrate how the present invention 12 provides maximum independent movement for maximum effective control. Each sphere joint 84a, 84b and 84c defines a cone 120a, 120b and 120c, respectively, of about 60° with the upper limit given by the stroke of the piston rods 82a, 82b and 82c. The cylinders 80a, 80b and 80c are mounted coaxially with the sphere joints 84a, 84b and 84c, thus allowing for direct connection to the three small air tubes or hoses 94a, 94b and 94c that pass through the sphere joints 84a, 84b and 84c, respectively. These details may be further appreciated by referring to FIG. 5E. Each cylindrical piston rod 82a, 82b and 82c is attached to the fingertips of the finger digits 62, 64 and 66 through the cylindrical joints that comprise the pins 110a, 110b and 110c that allow the maximum movement in the axial (i.e. two-dimensional) plane of the fingers 62, 64 and 66. The foregoing maximum movement is achievable by making the finger actuators 78a, 78b and 78c oppose the palm 58 from the other digits 62, 64 and 66. The freedom of movement is further enhanced by separating the sphere mounting blocks 90a, 90b and 90c with their housings 86a, 86b and 86c from each other as far as possible and by mounting the thumb digit actuator 78a on the short leg 116 of "L" shaped base 88, thereby putting it in a different plane with the other two actuators 78b and 78c, which are mounted on the long leg 118 of the "L" shaped base 88. The foregoing provides for maximum simulation of real feedback in a lifelike setting. For example, if the operator 34 were to direct the robot slave hand 18 to pick up an orange, the force feedback to the sensor glove 30 provided by the actuator system 28 would provide individual realistic feedback to each of the digits 62, 64 and 66. It will be appreciated from FIGS. 5C and 5D that each conic envelope 120a, 120b and 120c does not interfere significantly with the other. The sphere joints 84a, 84b and 84c provide for three degrees of freedom while the cylindrical pin bearings 110a, 110b and 110c provide for two degrees of freedom. It has been found that three feedback actuators 78a, 78b and 78c are sufficient to provide realistic response in view of the fact that the thumb, index and middle digits 62, 64 and 66, respectively, provide most of the manipulation of a hand. However, it would be possible to expand the system to provide feedback actuators 78 to the fourth or ring finger 68 and/or the little finger 70. Nevertheless, three to four actuators 78 are sufficient for most purposes because five fingers may provide too much redundancy.

The use of hook and loop material 98, 100, 104 and 106 such as the well known Velcro ® has two advantages. First, it allows the actuator system 28 to be removed completely from the sensor glove 30 so that the glove 30 can be used without the actuators 28. Second, and perhaps more importantly, it allows the actuator system 28 to be calibrated against each person's hand. In this manner, the attachment 28 to the glove 30 can be customized so that the fit is proper from operator to operator.

The prism-shaped wedge mounting sections 108a-c are important because they allow motion to the fingertips 62, 64 and 66 which is relatively normal to the fingertips. This is a more natural feeling since reaction forces on the human hand are more likely to be normal to the surface of the skin rather than parallel with respect thereto.

Prior art feedback actuators typically provided one degree of freedom. The present invention is much more flexible and provides both in and out manipulation as well as full lateral manipulation in the context of at least three to five independently operable actuators 78. The foregoing, since it fits within the palm of the glove 30, is relatively small and compact compared to prior art devices.

The Polhemus sensor 76 operates at 30 Hz and provides real time measurements of the position and orientation of the wrist of the glove 30.

Pressurized air with a pressure of up to 110 psi is applied through the manifold 48 and through valves 50, 52 and 54 to actuators 78a, 78b and 78c. It is possible that hydraulic pressure could also be used but it is not as convenient in the context since relatively low feedback forces are required. For applications of very high feedback forces, perhaps hydraulic fluids might be a possibility.

The use of a sphere joint 84a-c having a pneumatic fitting 92a-c that passes through the joint is very useful in the context of the present invention because it avoids any fixed resistance that could be due to lateral motion if the pneumatic hoses 94a, 94b and 94c were connected directly to the cylinders 80a, 80b and 80c. This further dramatically enhances the realistic independent "feel" of the actuator system 28.

In summary, the actuator system 28 provides real pressure feedback to a sensor glove 30. Also important is the fact that the actuator system 28 is very lightweight and in its entirety weighs about 45–50 grams (i.e. approximately 0.1 pounds). The use of plastic and other lightweight materials can further reduce the weight of the actuator system 28 to the point where the operator 34 barely notices its presence.

Figure 6:
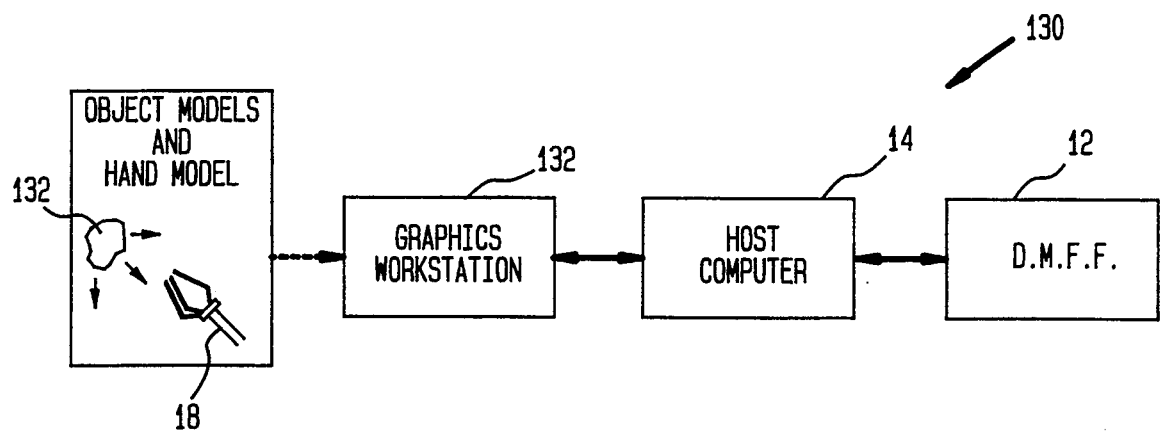
FIG. 6 illustrates an alternative embodiment of the actuator system in the context of an artificial or virtual reality environment.

The actuator system 28 in conjunction with the D.M.F.F. 12 can be used in environments other than that described in FIG. 1. For example, the system can be used as part of an artificial reality environment 130 as illustrated in FIG. 6. In the artificial reality environment 130, the D.M.F.F. 12 interacts with a host computer 14 as previously described. The output thereof provides an input to a graphics workstation 132 which, with the appropriate instructions, controls a pseudo robot slave hand or model of a human hand 18 and pseudo objects 132. The artificial feedback from the graphics workstation 132 returns to the host computer 14 and is provided to the D.M.F.F. 12 in the form of an artificial force feedback in response to the pseudo environment generated by the graphics workstation 132 and the host computer 14. The response of the D.M.F.F. 12 is, however, the same for the artificial force feedback, as in a real environment.

Figure 7:
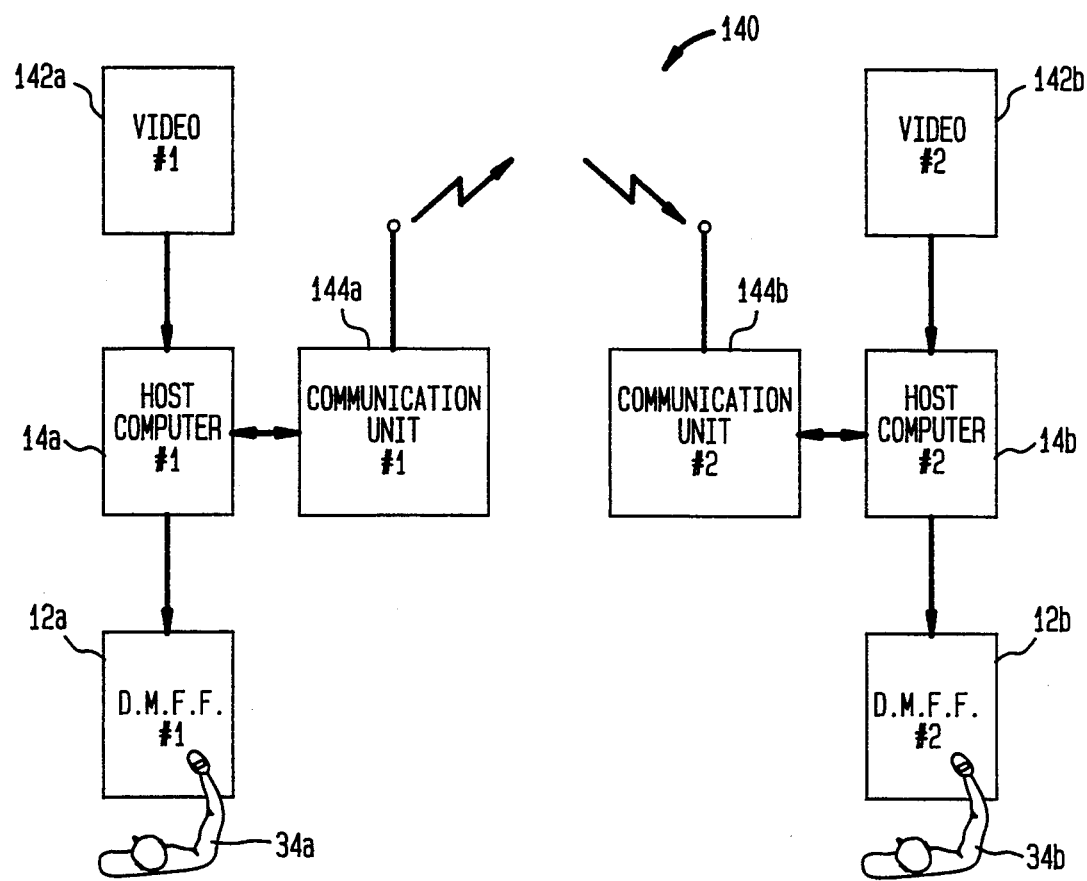
FIG. 7 illustrates another alternative embodiment of the actuator system in the context of a teleconferencing environment.

Another interesting alternative environment for the D.M.F.F. 12 and the actuator system 28 is shown in FIG. 7. A teleconferencing environment 140 is illustrated in which an operator 34a manipulating a first D.M.F.F. 12a can virtually shake hands with another operator 34b using a second D.M.F.F. 12b. The first operator 34a, manipulating the first D.M.F.F. 12a provides input to a first host computer 14a and the output thereof is transmitted by a first communications unit 144a. Signals are received by a second communications unit 144b and are transmitted to a second host computer 14b which in turn supplies signals to a second D.M.F.F. 12b and a second video monitor 142b. The first video monitor 142a, including a camera in both instances, is likewise connected to the first host computer 14a. In operation, the teleconferencing environment 140 might operate as follows. The first operator 34a manipulating the first D.M.F.F. system 12a might reach out to shake hands with the second operator 34b employing the second D.M.F.F. 12b. The first operator 34a can see the second operator 34b on the video camera and monitor system 142a. The reaching out motion is interpreted by the first host computer 14a and transmitted by the first communications unit 144a. The signals are received by the second communications unit 144b and transmitted to the second host computer 14b. A picture of the first operator 34a will appear on the second video monitor 142b. Simultaneously, the second D.M.F.F. 12b will produce a gripping motion similar to that produced by the first operator 34a on the first D.M.F.F. 12a. In response thereto, the second D.M.F.F. operator 34b will feel the simulated motion of the first operator 34a and, will probably reciprocate by returning the hand clasp which will be interpreted by the second host computer 14b and transmitted via the second communications unit 144b to the first communications unit 144a and interpreted by the first host computer 14a as a force feedback to the first operator 34a via the first D.M.F.F. system 12a. In the foregoing fashion, it is possible for the first operator 34a to shake hands with the second operator 34b and the second operator 34b to shake hands with first operator 34a in a manner that simulates the realistic tactile sensations of the actual handshaking experience. Subsequently, both operators, 34a and 34b, may interact with an object, for example, a textile sample to be sold. They both "feel" it and then negotiate the sale.

Figure 8B:
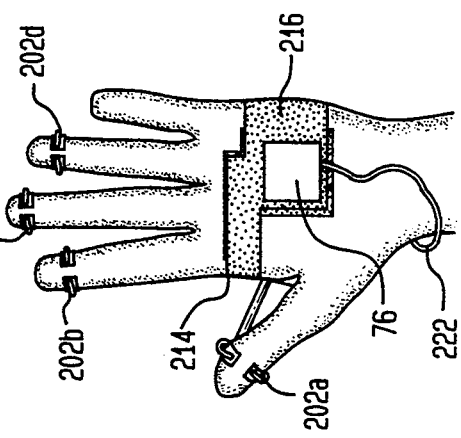
FIG. 8B is a rear elevational view of the actuator system illustrated in FIG. 8A.
Figure 8C:
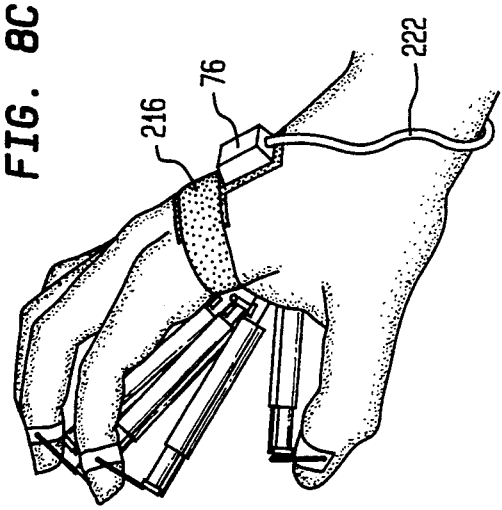
FIG. 8C is a lateral view of the actuator system illustrated in FIGS. 8A and 8B.
Figure 8A:
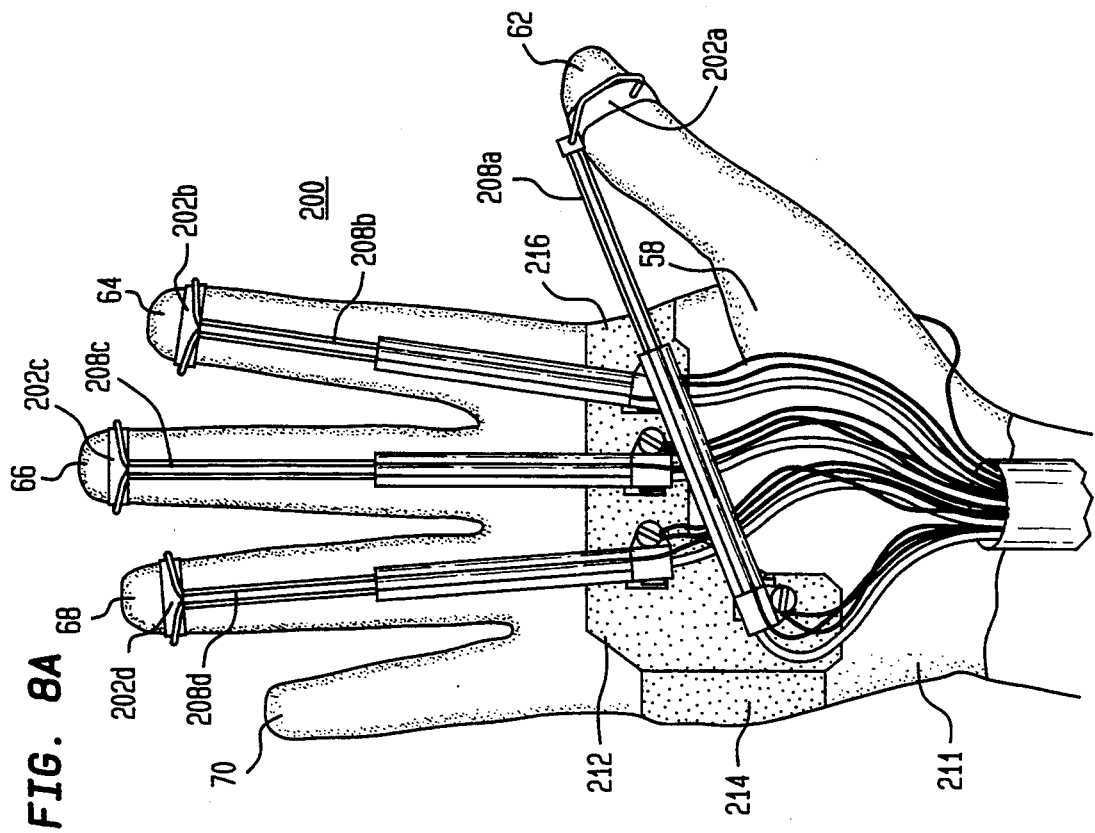
FIG. 8A is a front elevational view of an alternative actuator system attached to a portable palm mount.

An alternative actuator system 200 is shown in FIGS. 8A–8C. Actuator system 200 is located in the palm and comprises four actuators 208a, 208b, 208c and 208d which can apply pressure from palm 58 against the thumb digit 62, index digit 64, middle digit 66 and ring finger digit 68, respectively. Actuator system 200 is mounted on an L-shaped base 212. L-shaped base 212 is similar to previously described L-shaped base 88. A first hook and loop belt 214 wraps around palm 85 and attaches to L-shaped base 212. A second hook and loop belt 216 attaches to glove 211 and mates with first belt 214. Actuator system 200 is used without a dextrous master glove, as it has its own sensing means.

Figure 10:
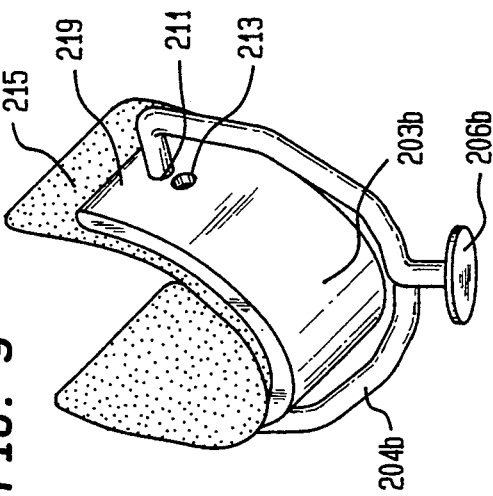
FIG. 10 is a perspective view of the digit mounted connected to a cylinder and a digit.
Figure 9:
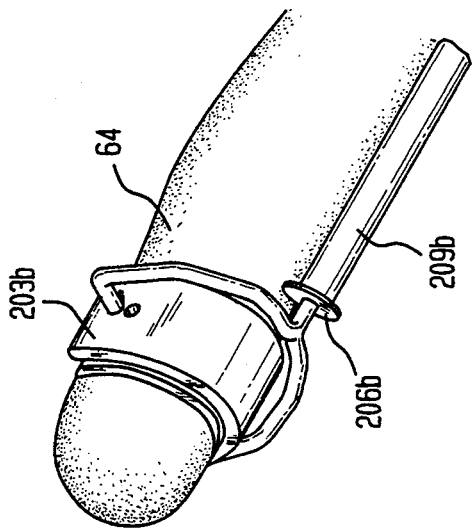
FIG. 9 is a perspective view of a digit mount used in the actuator system.
Figure 11:
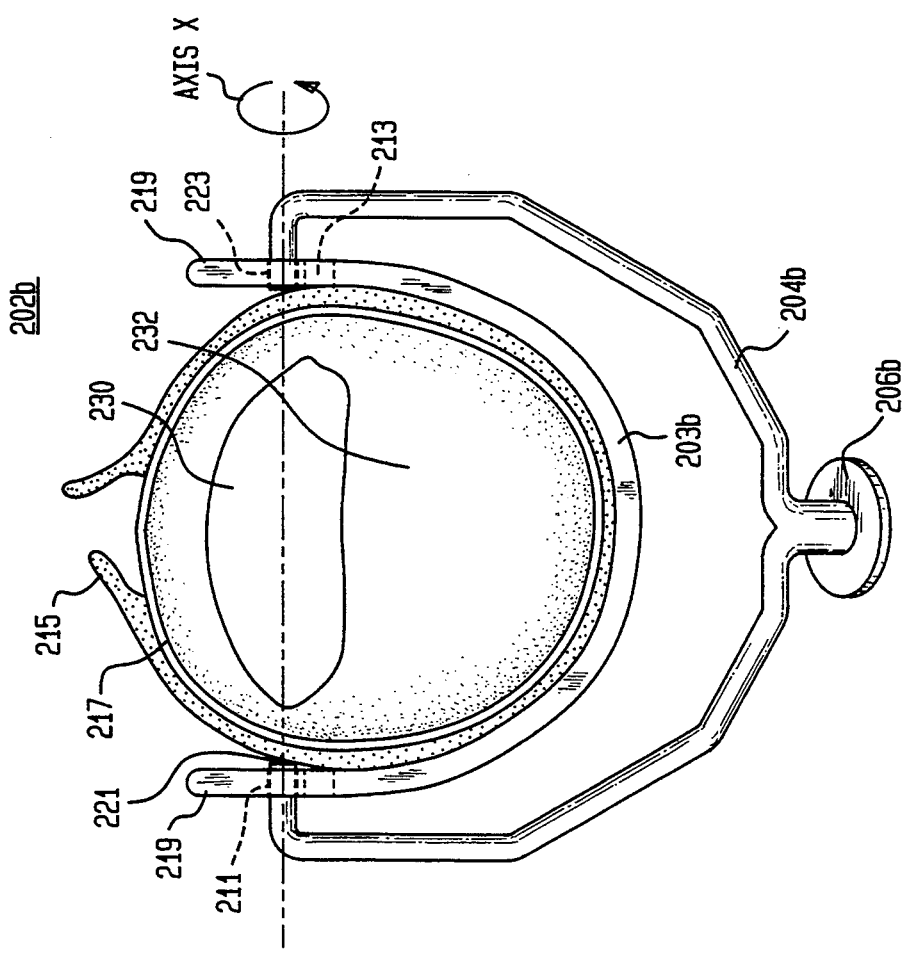
FIG. 11 is a front elevational view of the finger mount illustrated in FIG. 9.

Digit mounts 202a, 202b, 202c and 202d attach actuator system 200 to the thumb digit 62, index digit 64, middle digit 66 and ring finger digit 68, respectively. As shown in FIGS. 9–11, digit mount 202b includes belt 215 for attachment to digit 64. Belt 217 mates with belt 215. Preferably belts 215 and 217 are formed of well known Velcro ® material. Finger tip 232 and a portion of nail 230 extend from one end of belt 215. A flexible band 203b is mounted to belt 215. Flexible band 203b has a semicircular shape. Preferable, flexible band 203b is formed of a plastic material. Frame 204b has a semicircular fork shape and is positioned beneath flexible band 203b. A pair of holes 211, 213 are positioned at end 219 on either side of flexible band 203b. Frame 204b is attached to one of holes 211 or 213 on either side of flexible band 203b. Holes 211, 213 allow for adjustment of digit mount 202b depending on the size of the digits. If a small digit is used (i.e., finger digit) frame 203b is mounted in hole 213 and if a large digit is used (i.e., thumb digit) frame 203b is mounted in hole 211. Frame 204b is attached to connector 206b. Connector 206b mounts to sensor shaft 209b of actuator 208b. Frame 204b is preferably rigid and is formed of a wire or metal material. Force is applied from actuator system 208b to points 221 and 223 of frame 204b in an upward direction from axis X.

Figure 12:
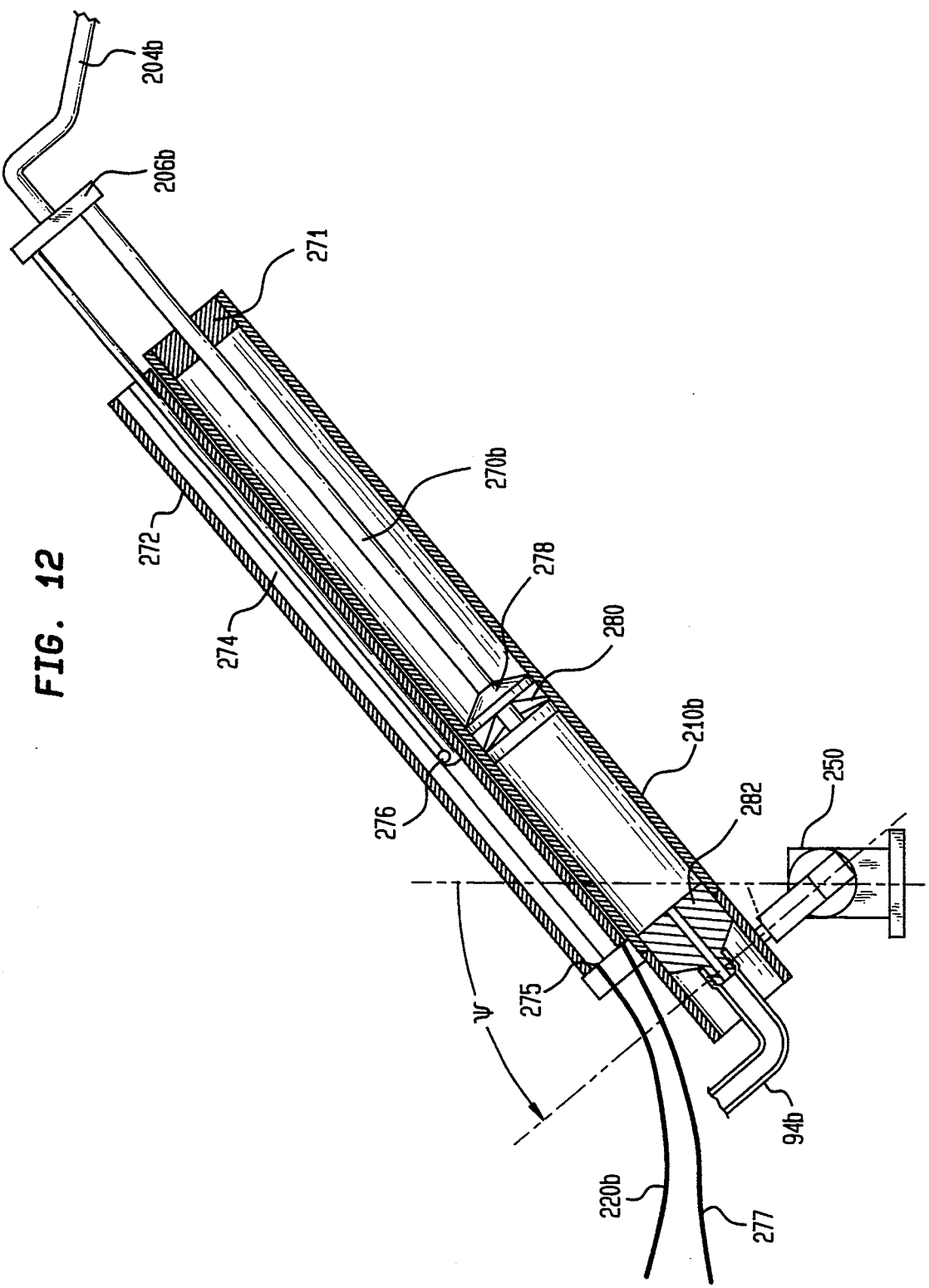
FIG. 12 is a side elevational cross-sectional view of a pneumatic cylinder of the actuator system shown in FIGS. 8A–8C.

FIG. 12 illustrates actuator system 208b. A cylinder is mounted to mount 250. Details of mount 250 are described in FIGS. 13A–E. Pneumatic hose 94b extends into cylinder hose adapter 282. Upon application of pneumatic pressure to pneumatic hose 94b piston 278, gasket 280 and shaft 270b move toward a cylinder cap 271 thereby providing a feedback force to frame 204b of digit mount 202b. Linear position sensor 272 measures the movement or displacement of the digit. Preferably, linear position sensor 272 is a potentiometer. Contact 276 moves along carbon film 274 upon movement of cylinder shaft 270b. The resistance value of linear position sensor 272 changes depending on the length of carbon film 274 between contact 276 and contact 275. The resistance value can be used to determine the position of connector 206b. A signal 277 of the resistance value is relayed through interface line 220b to the actuator interface 400. Alternatively, linear position sensor 272 can be a capacitor, Hall effect sensor or a linear differential transformer. It will be appreciated that other sensors that are known in the art could be used for linear position sensor 272.

Figure 13C:
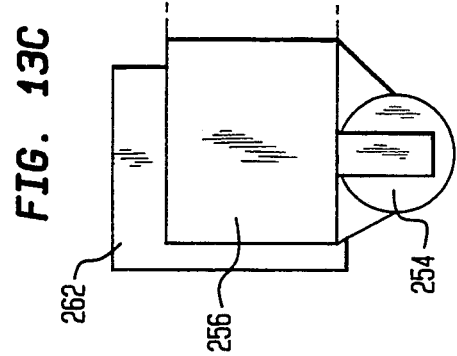
FIG. 13C is a top view of the azimuthal sensor mount.
Figure 13E:
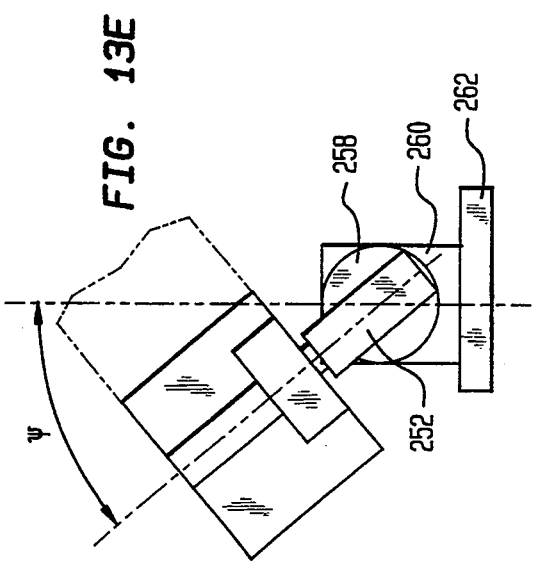
FIG. 13E is a lateral view of the azimuthal mount showing declination rotation angle $\psi$.
Figure 13B:
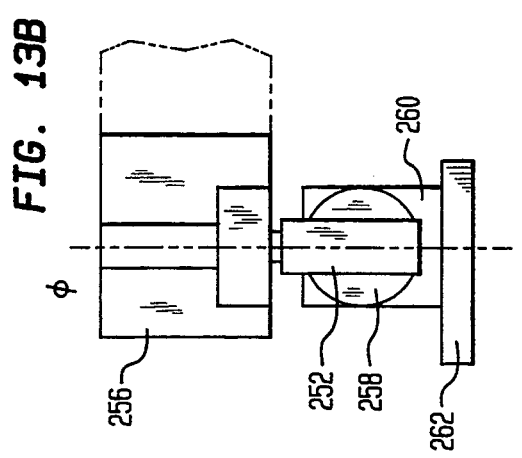
FIG. 13B is a lateral view of the azimuthal sensor mount.
Figure 13D:
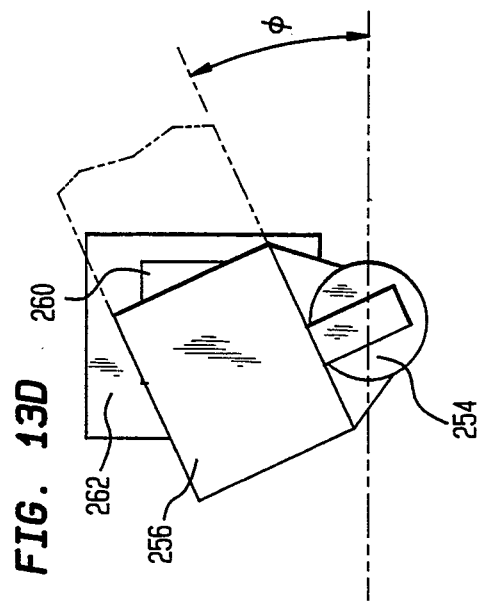
FIG. 13D is a top view of the azimuthal sensor mount showing azimuthal rotation angle $\phi$.
Figure 13A:
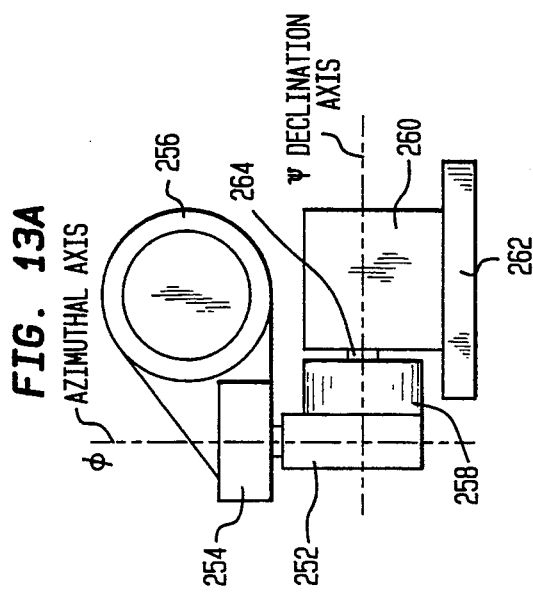
FIG. 13A is a front view of an azimuthal sensor mount according to the present invention.

FIGS. 13A–E illustrate mount 250. Mount 250 provides two degrees of freedom to each cylinder body 210b in the "yaw" and "pitch" direction. Rotation angles of cylinder body 210b are defined by a declination angle $\psi$ and azimuthal angle $\phi$. Rotary position sensor 252 measures the azimuthal angle $\phi$ and rotary position sensor 260 measures the declination angle. Typically rotary position sensors 252 and 260 are capacitors, Hall effect sensors, and rotary variable differential transformers. Preferably rotary position sensors 252 and 260 are potentiometers. Rotary position sensor 260 is mounted on base 262, as shown in FIG. 13A. Mount housing 258 surrounds joint 264 and is connected between rotary position sensors 252 and 260. Housing block 254 attaches rotary position sensor 252 to cylinder 210b and linear position sensor 272. The measurements for linear position, declination angle $\phi$ and azimuthal angle $\psi$ represent information for calculating the position of the tips of the digits relative to base 212.

Polhemus sensor 76 provides information with respect to the orientation position of the wrist. Polhemus sensor 76 is attached to the back of hand with belt 216. Hand orientation information is relayed through line 222 to actuator interface 400 described in FIG. 17.

Figure 14:
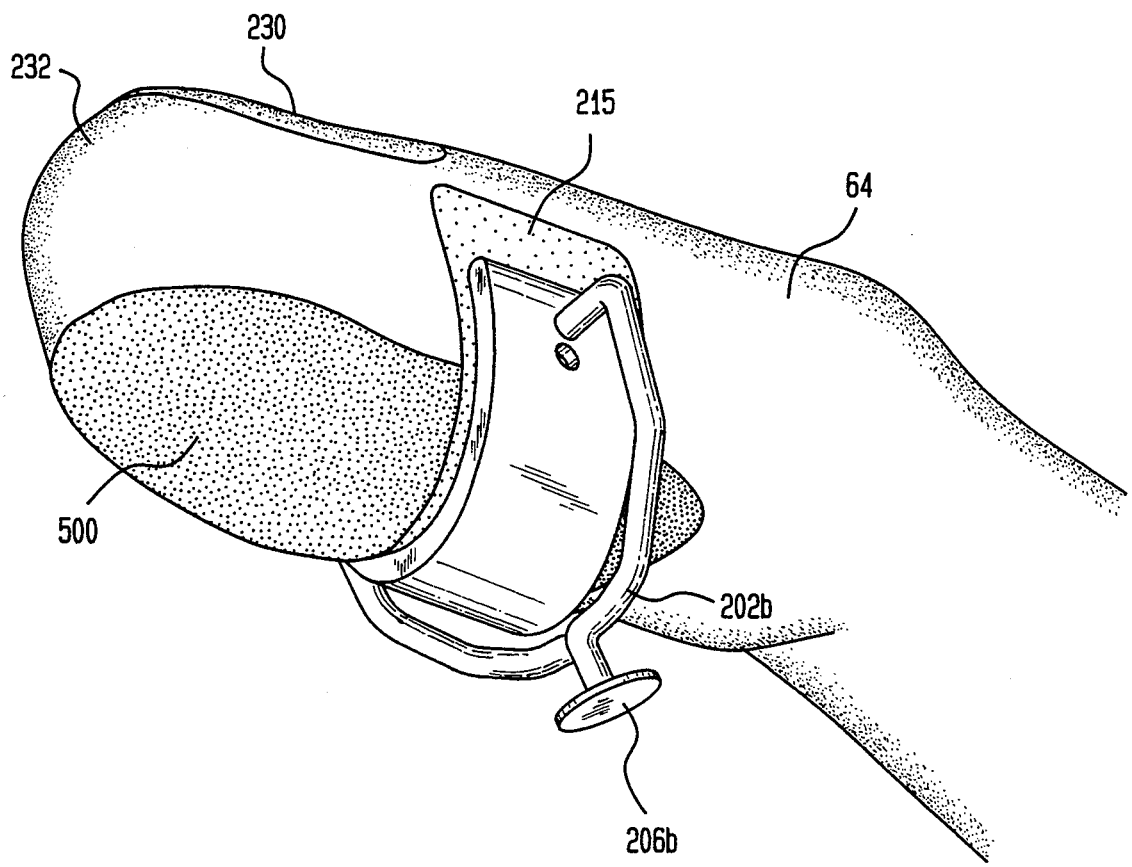
FIG. 14 is a perspective view of digit mount used with a touch feedback array.

FIG. 14 is a perspective view of an additional feature of the present invention, the use of digit mount 202b with a touch feedback array. A touch feedback array 500 is placed on the lower surface of finger tip 232. Feedback array 500 extends underneath finger mount 202b. The force feedback to finger mount 202b does not interfere with the placement of touch feedback array 500 as the force feedback is applied to finger mount 202 above feedback array 500.

Figure 15:
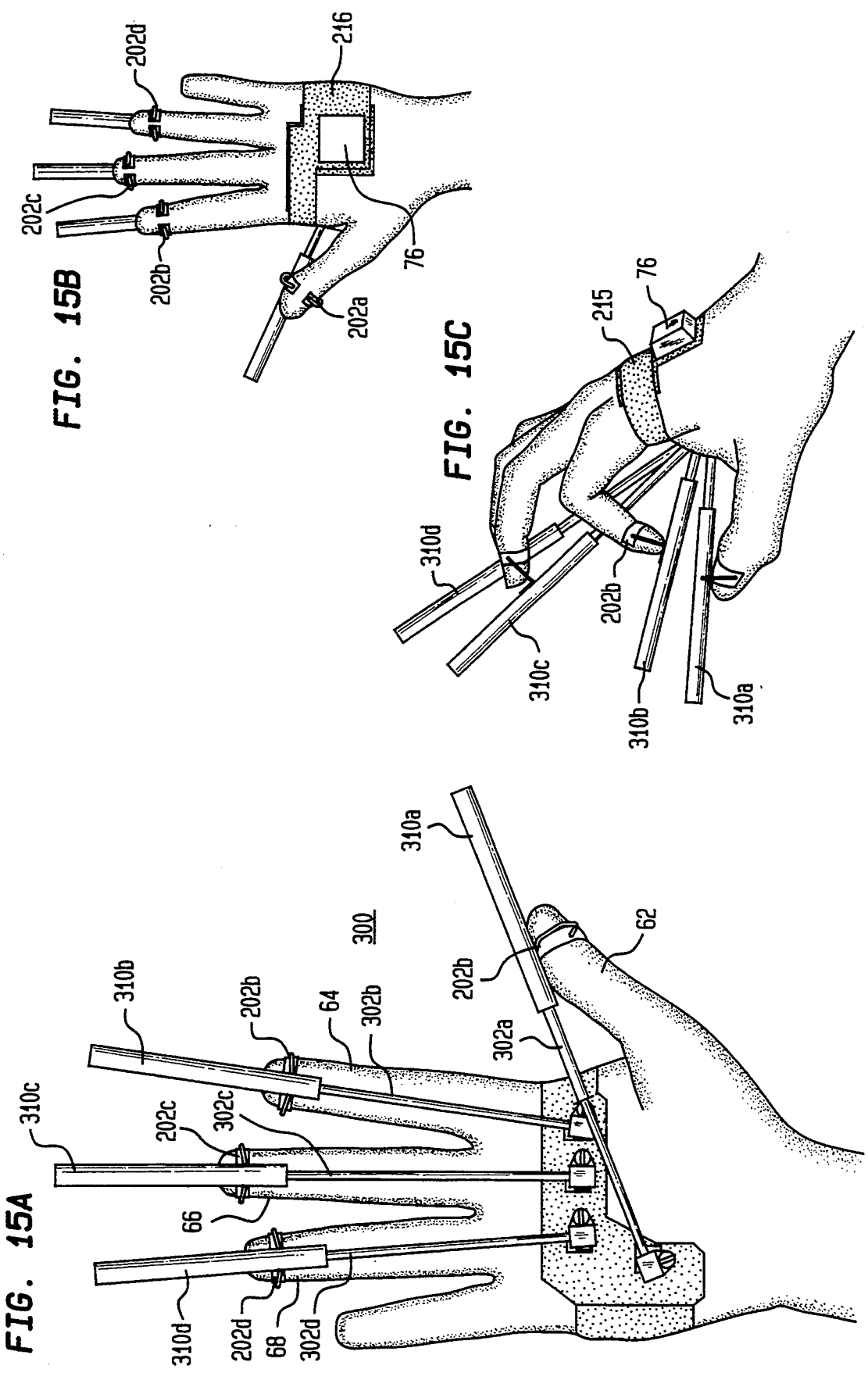
FIG. 15A is a front elevational view of an actuator system with extended cylinders.
FIG. 15B is a back elevational view of the actuator system shown in FIG. 15A.
FIG. 15C is a lateral view of the actuator system shown in FIGS. 15A and 15B.

FIGS. 15A–C describe an alternative embodiment of actuator system 202 including extended range of motion for the actuator system. Actuator system 300 provides increased range of motion for actuators 302a–d by providing extended actuator cylinder bodies 310a–d. Extended cylinder bodies 310a–d extend a distance beyond digit mounts 202a–d. Preferably extended cylinder bodies 310a–d extend about 0.5 to about 3.0 inches from the tip 232 of digits 62, 64, 66 and 68. As described in FIG. 15C, extended actuator cylinder bodies 310a–d allow digits 62, 64, 66 and 68 to be moved closer to the palm than do cylinder bodies shown in FIG. 8C. Extended actuator cylinders 310a–b provide at least twice the range of motion of the cylinder bodies in FIG. 8C.

Figure 16:
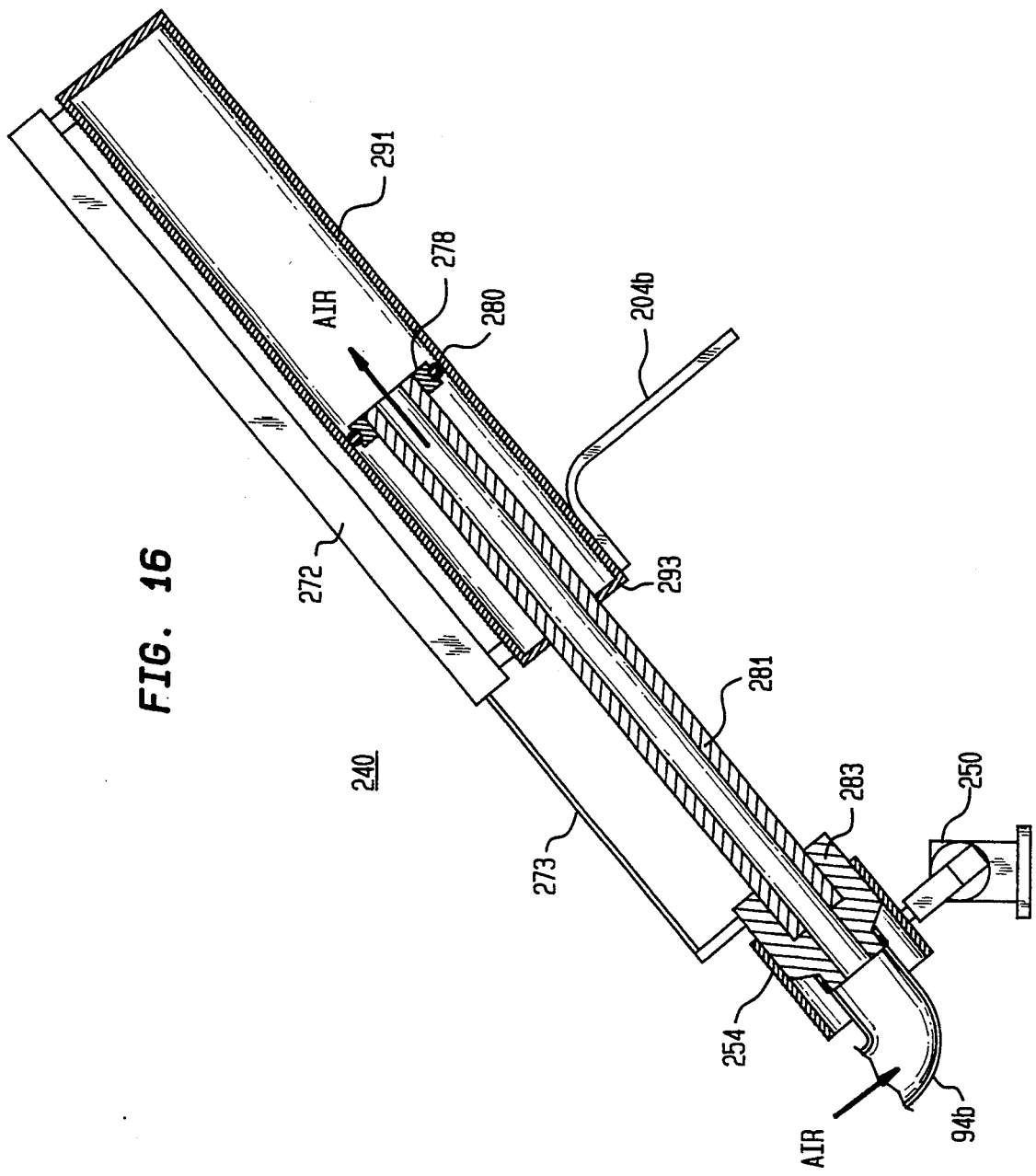
FIG. 16 is a side elevational cross-sectional view of a cylinder and linear position sensor used with the actuator system shown in FIGS. 15A–C.

FIG. 16 illustrates a cylinder adapter 290 used with actuator system 300. Hose adapter 283 connects activator 290 for azimuthal housing block 254 of mount 250. Shaft extension 273 connects linear position sensor 272 to hose adapter 283. Pneumatic pressure flows through hollow shaft 281. Cylinder 291 moves along shaft 281 upon application of pneumatic pressure for pneumatic hose 94b. Linear position sensor 272 moves together with cylinder 291 along shaft 273. Finger mount 204b is connected to end 293 of cylinder 291, thereby providing a force feedback to frame 204b of digit mount 202b.

Figure 17:
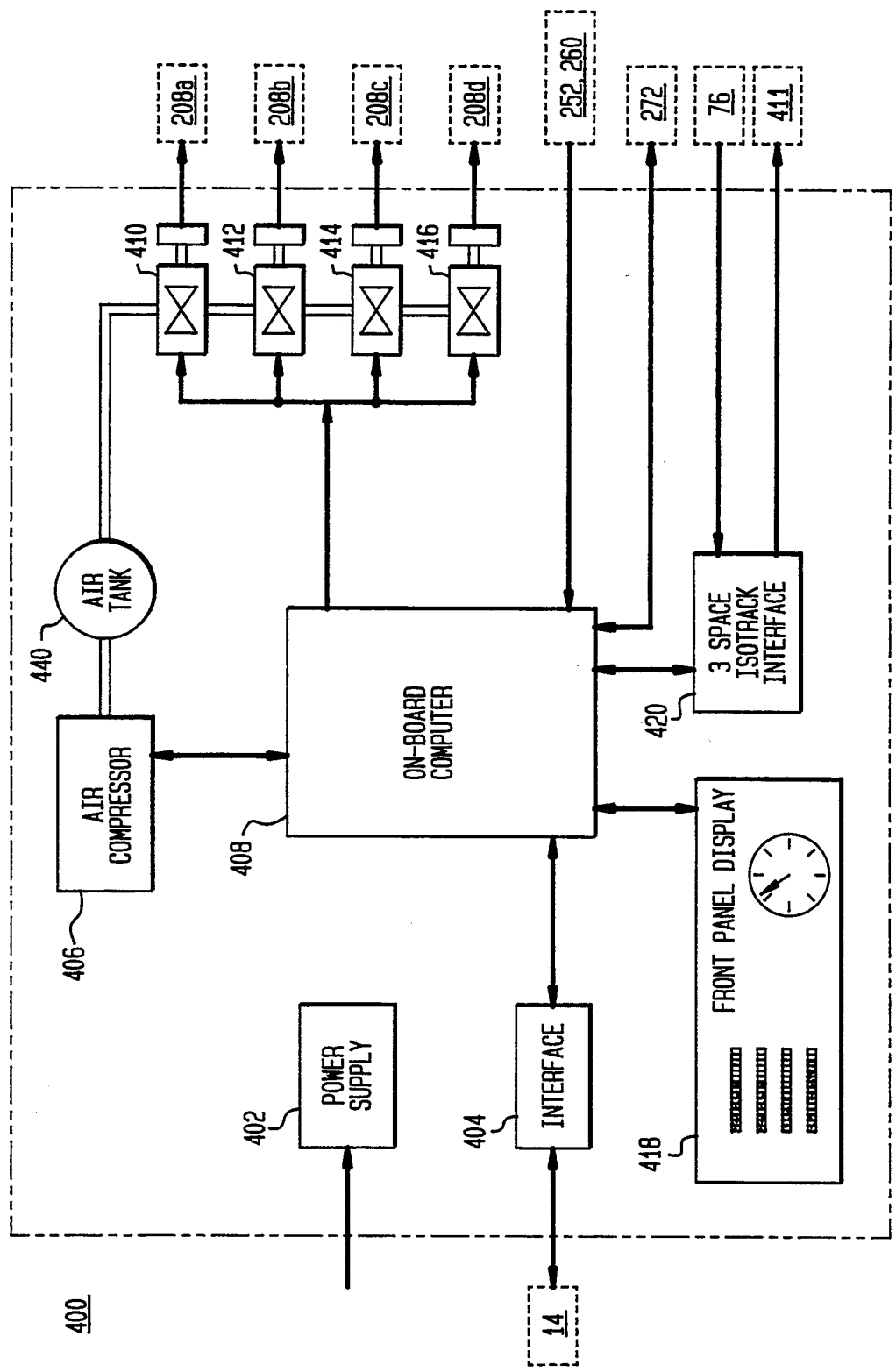
FIG. 17 is a schematic diagram of an interface for use with the actuator system shown in FIGS. 8A–8C and 15A–15C.

Details of actuator interface 400 is shown in the schematic diagram of FIG. 17. Signals from linear position sensor 272 and rotary position sensors 252 and 260 are received at an I/O port of on board computer 408. Signals from polhemus sensor 76 are received at polhemus interface 420. Polhemus interface 420 communicates with polhemus reference source 411, polhemus sensor 76 and with on-board computer 408. On-board computer 408 passes a control signal to pressure regulators 410, 412, 414 and 416 to control air pressure to actuators 208a, 208b, 208c and 208d, respectively. Air pressure is provided from air compressor 406 to pressure regulators 410, 412, 414 and 416.

A compressor control module controls air compressor 406 and air tank 440 for providing air to pneumatic regulators 410, 412, 414 and 416.

On board computer 408 communicates with a front panel display 418. Front panel display 418 includes LED output to display the pressure of air in actuator system 200. Power supply 402 supplies power to air compressor 406, pressure regulators 410, 412, 414, 416, on board computer 408 and polhemus interface 420. Interface 404 connects a communication port of host computer 14 to on board computer 408. Preferably, actuator interface 400 is a "stand alone" unit.

Figure 18:
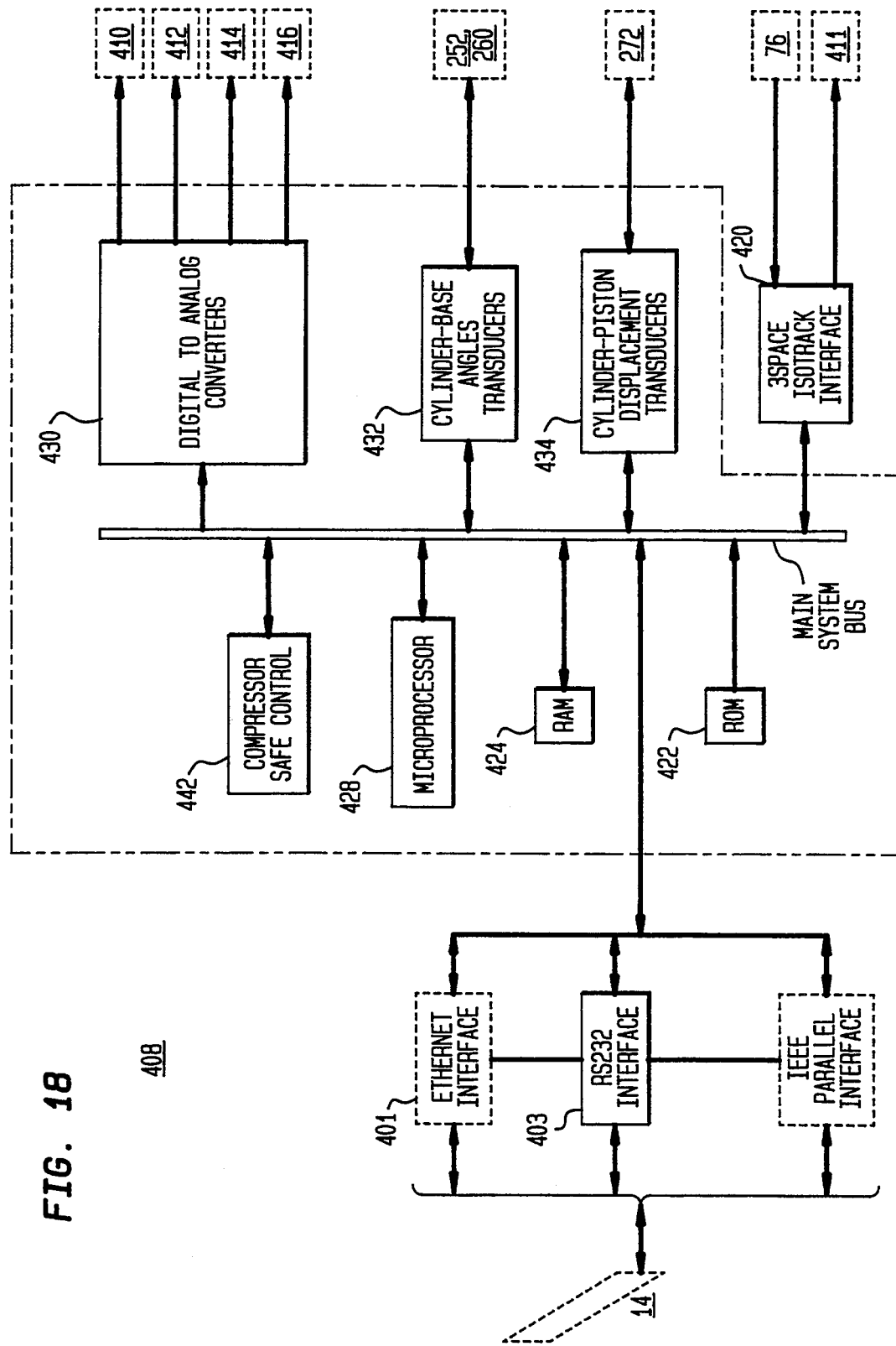
FIG. 18 is a detailed schematic diagram of the interface shown in FIG. 17.

FIG. 18 illustrates details of on board computer 408. Analog signals from linear position sensor 272 are applied to cylinder piston displacement transducer 432 and analog signals from rotary position sensors 252 and 260 are applied to cylinder angle transducer 434 for forming digital signal information. Output from cylinder base angles transducers 432 and 434 can be stored in buffers in RAM 424. I/O routines and computer commands are stored in ROM 422. A microprocessor 428 controls operation of a board computer 408. On board computer 408 includes a digital to analog convertor 430 for converting digital signals from an on-board computer 408 into analog signals for controlling pressure regulators 410, 412, 414 and 416.

An ethernet interface 401, RS232 interface 403 and IEEE parallel interface 405 can be used to communicate information to host computer 14.

Figure 19:
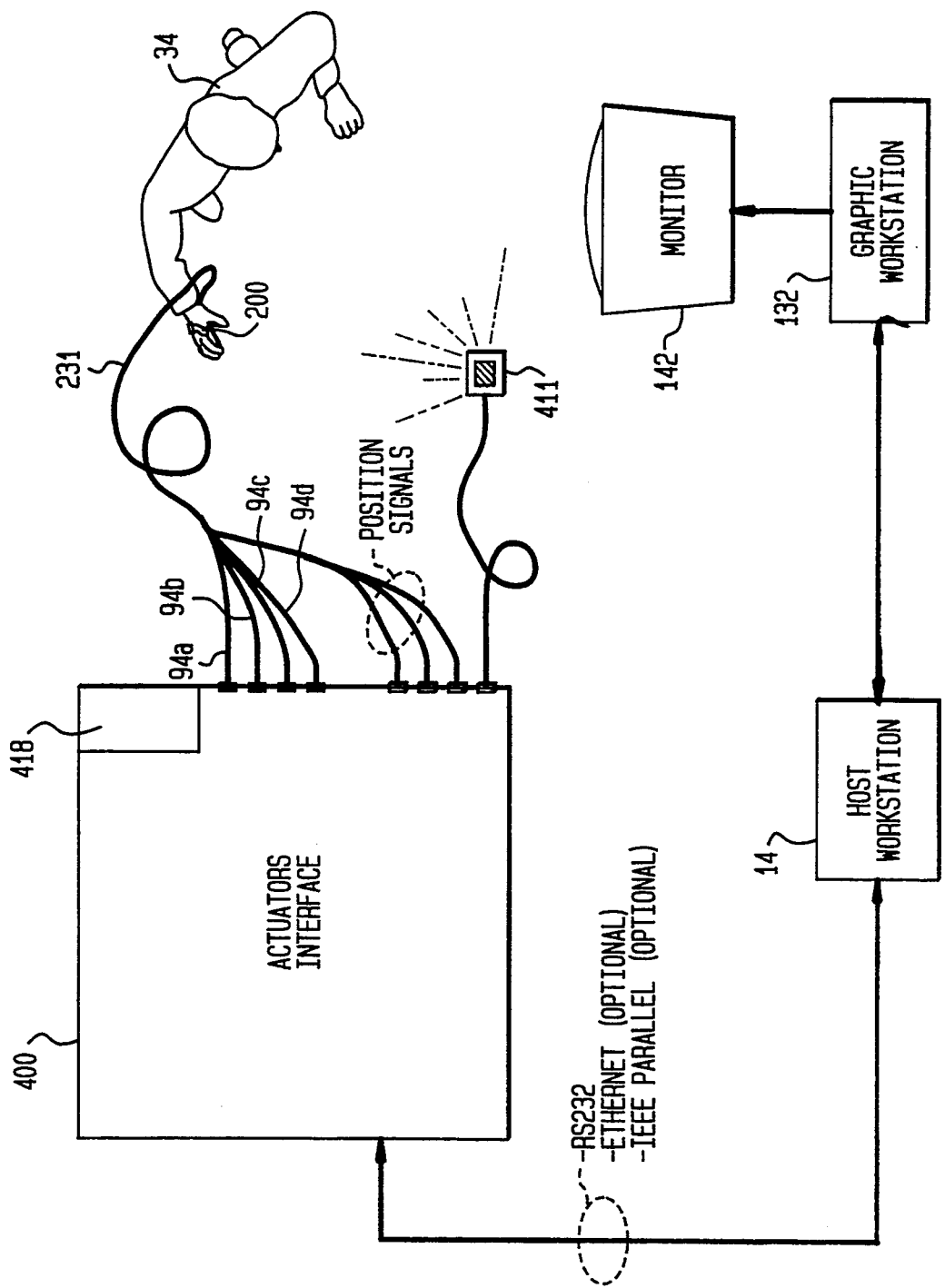
FIG. 19 illustrates the actuator system of FIGS. 8A–8C and 15A–15C in a virtual reality environment application (simulation).

Actuator system 200 in conjunction with user's virtual environment is illustrated in FIG. 19. Monitor 142 can display a virtual environment simulation. Monitor 142 interacts with graphic workstation 132 which receives and transmits information to host work station 14. If complexity of the on-board computer is increased, the host computer 14 and the graphics workstation can be omitted. This feature provides a low cost, portable, self-contained, virtual reality system. The on-board computer can be equipped with graphics acceleration cards, a monitor interface and extra hardware to increase computation power.

In summary, actuator system 200 provides real pressure feedback to a digit mount without using a dextrous sensing glove. The system includes linear position sensors and a pair of rotary position sensors for sensing the position of the digits with respect to the palm support. Digit mounts can be used without interfering with a touch feedback array. Extended cylinder shafts have the advantage of increased range of motion of the actuator system. The system has the advantage of being operable without the use of a dextrous master glove.

While the invention has been described with reference to the preferred embodiment thereof, it will be appreciated by those of ordinary skill in the art that modifications can be made to the structure and functions of the system without departing from the spirit and scope of the invention as a whole.

We claim:

1. An actuator system for placement in a hand comprising:
   a first digit support connectable to a first digit of said hand;
   a palm support spaced from said first digit and positionable on the palm surface of said hand;
   a first sensor means for generating electrical signals attached to said first digit support and a first actuator means and responsive to movement of said first digit;
   said first actuator means extending between said first digit support and said palm support for providing force feedback to said first digit support as a result of said electrical signals generated by said first sensor means;
   a first mount for connecting said first actuator means to said palm support; and
   a first rotary sensor means attached to said first mount for measuring rotation of said first actuator means wherein said first rotary sensor measures an azimuthal angle $\psi$ and a declination angle $\phi$.

2. The system of claim 1 wherein said first actuator means comprises a first pneumatic cylinder.

3. The system of claim 1 further comprising:
   a second digit support connectable to a second digit of said hand;
   a second sensor means for generating electrical signals attached to said second digit support and a second actuator means and responsive to movement of said second digit;
   said second actuator means extending between said second digit support and said palm support for providing force feedback to said second digit support as a result of said electrical signals generated by said second sensor; and
   a second mount for connecting said second actuator means to said palm support and a second rotary sensor means attached to said second mount for measuring rotation of said second actuator means wherein said second rotary sensor measures an azimuthal angle $\psi$ and a declination angle $\phi$.

4. The system of claim 3 wherein said second actuator means comprises a pneumatic cylinder.

5. The system of claim 3 further comprising:
   a third digit support connectable to a third digit of said hand;
   a third sensor means for generating electrical signals attached to said third digit support and a third actuator means and responsive to movement of said third digit;

said third actuator means extending betweens said third digit support and said palm support for providing force feedback to said third digit support as a result of said electrical signals generated by said third sensor; and a third mount connected between said third actuator means and said palm support and a third rotary sensor means attached to said third mount for measuring rotation of said third actuator means wherein said third rotary sensor measures an azimuthal angle $\psi$ and a declination angle $\phi$.

6. The system of claim 5 wherein said third actuator means comprises a pneumatic cylinder.

7. The system of claim 5 further comprising:
a fourth digit support connectable to a fourth digit of said hand;
a fourth sensor means for generating electrical signals attached to said fourth digit support and a fourth actuator means and responsive to movement of said fourth digit;
said fourth actuator means extending between said fourth digit support and said palm support for providing force feedback to said fourth digit support as a result of said electrical signals generated by said fourth sensor; and
a fourth mount for connecting said fourth actuator means to said palm support and a fourth rotary sensor means attached to said fourth mount for measuring rotation of said fourth actuator means wherein said fourth rotary sensor measures an azimuthal angle $\psi$ and a declination angle $\phi$.

8. The system of claim 7 wherein said fourth actuator means comprises a pneumatic cylinder.

9. The system of claim 7 further comprising:
attachment means for selectively attaching said palm support to said hand.

10. The system of claim 9 wherein said attachment means comprises a first material for selectively mating with a second material,
wherein one of said materials comprises a hook-type material and said other type of material comprises a loop-type material for mating with said hook-type material.

11. The system of claim 10 wherein said palm support has a generally "L" like shape having a first and a second leg,
wherein one of said mounts is mounted on said first leg and the remaining mounts are mounted on said second leg of said palm support.

12. The system of claim 11 wherein said digits supports comprising:
first, second, third and fourth digit mounting means pivotally connecting said first, second, third and fourth actuator means and said first, second, third and fourth digits.

13. The system of claim 12 wherein said first, second, third and fourth mounting means respectively comprise:
a flexible band having holes therein;
a semicircular frame connected into the holes of said flexible band; and
a material connected to said flexible band having a front surface formed of a hook type material and rear surface formed of a loop type material.

14. The system of claim 13 further comprising a touch feedback array attached to the tip of said digits beneath said digit supports.

15. The system of claim 14 wherein said first, second, third and fourth actuators extend beyond said first, second, third and fourth digits, respectively.

16. The system of claim 15 wherein said system further comprises virtual reality environment means for connection to said actuators and said sensor means.

* * * * *